US006399784B2

(12) United States Patent
Ma et al.

(10) Patent No.: US 6,399,784 B2
(45) Date of Patent: Jun. 4, 2002

(54) EFFICIENT METHOD FOR THE CONVERSION OF NITRILES TO AMIDINES

(75) Inventors: Philip Ma, Chadds Ford, PA (US); Pasquale N. Confalone, Wilmington; Hui-Yin Li, Newark, both of DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/757,459

(22) Filed: Jan. 10, 2001

Related U.S. Application Data

(62) Division of application No. 09/346,409, filed on Jul. 1, 1999, which is a division of application No. 09/166,722, filed on Oct. 5, 1998, now Pat. No. 5,962,693.
(60) Provisional application No. 60/061,707, filed on Oct. 6, 1997.

(51) Int. Cl.[7] .................... C07D 261/02; C07D 261/08; C07C 257/18

(52) U.S. Cl. ...................... 548/240; 548/247; 548/131; 558/375; 564/163; 564/244; 564/246

(58) Field of Search ................................ 548/240, 247, 548/131; 514/378; 564/163, 244

(56) References Cited

U.S. PATENT DOCUMENTS

| | | | | | |
|---|---|---|---|---|---|
| 5,187,157 | A | * | 2/1993 | Kettner et al. ................. | 514/18 |
| 5,227,490 | A | * | 7/1993 | Hartman et al. ............. | 514/371 |
| 5,446,056 | A | | 8/1995 | Wityak et al. | |
| 5,484,946 | A | | 1/1996 | Abood et al. | |
| 5,559,127 | A | * | 9/1996 | Hartman et al. ............ | 514/322 |
| 5,849,736 | A | * | 12/1998 | Wityak et al. ............ | 514/227.8 |

FOREIGN PATENT DOCUMENTS

| | | |
|---|---|---|
| WO | 9514682 | 1/1995 |
| WO | 9514683 | 1/1995 |

OTHER PUBLICATIONS

Judkins et al., A Versatile Synthesis of Amidines From Nitriles via Amidoximes, *Synthetic Communications*, vol. 26(23), 4351–4367, 1996.
Eloy et al., "Amidoximes and Related Compounds", *Chem. Rev.*, vol. 62, pp. 155–183, 1962.
Barnard et al., "Heterocyclic Imines and Amines. Part 19. Isoquinoline and Other Products from α–o–Dioxyanostilbene and Basic Reagents", *J. Chem. Soc., Perkin Trans. I*, pp. 1813–1818, 1983.
Sanghvi et al., "Synthesis of Certain 4–Substituted–1–β–D–Ribofuranosyl–3–Hydroxypyrazoles Structurally Related to the Antibiotic Pyrazofurin", *Nucleosides & Nucleotides*, vol. 6(4), 737–759, 1987.
Chauhan et al., "Synthesis of 2,8–Diamidinobenz [b, f] oxepin & Related Compounds as Potential Leishmanicides", *Indian Journal of Chemistry*, vol. 22B, pp. 898–900, 1983.

Zhang et al., "The Chiral Specific Synthesis of DMP 754, a Platelet GP IIb/IIIa Antagonist", *Tetrahedron Letters*, vol. 37, No. 26, pp. 4455–4458, 1996.
Korbonits et al., "Ring Transformation of 1,2–Disubstituted 4(1H)—Quinazolone Oximes to 3,5–Disubstituted 1,2, 4–Oxadiazoles", *Chem. Ber.*, 122, pp. 1107–1112, 1989.
Andres et al., "Synthesis of Ribonucleosides of 4–(5)–Cyano–5(4)–Methylimidazole and Related 4–Substituted–5–Methylimidazole Ribosides", *J. Heterocyclic Chem.*, vol. 23, pp. 679–694, 1986.
Chiou et al., "A Simplified Procedure for Preparing 3,5–Disubstituted–1,2,4–Oxadiazoles by Reaction of Amidoximes with Acyl Chlorides in Pyridine Solution", *J. Heterocyclic Chem.*, vol. 26, pp. 125–128, 1989.
Santilli et al., "Synthesis of 2–Guanyl–4–(3–substituted–phenyl)thiazoles with Potent Histamine $H_2$–Antagonism Activity", *J. Heterocyclic Chem.*, vol. 28, pp. 2025–2028, 1991.
Petrie et al., "Synthesis and Biological Activity of Certain Nucleoside and Nucleotide Derivatives of Pyrazofurin", *J. Med. Chem.*, vol. 29, pp. 268–278, 1986.
Bedford et al., Nonquaternary Cholinesterase Reactivators. 3. 3(5)–Substituted 1,2,4–Oxadiazol–5(3)–aldoximes and 1,2,4–Oxadiazole–5(3)–thiocarbohydroximates as Reactivators of Organophosphonate–Inhibited Eel and Human Acetylcholinesterase in Vitro, *J. Med. Chem.*, vol. 29, pp. 2174–2183, 1986.
Weller et al., "Orally Active Fibrinogen Receptor Antagonists. 2. Amidoximes as Prodrugs of Amidines", *J. Med. Chem.*, vol. 39, pp. 3139–3147, 1996.
Unangst et al., "Novel 1,2,4–Oxadiazoles and 1,2,4–Thiadiazoles and Dual 5–Lipoxygenase and Cyclooxygenase Inhibitors", *J. Med. Chem.*, vol. 35, pp. 3691–3698, 1992.
Swain et al., "Novel 5–$HT_3$ Antagonists. Indole Oxadiazoles", *J. Med. Chem.*, vol. 34, pp. 140–151, 1991.
Ramasamy et al., "Total Synthesis of 2'–Deoxytoyocamycin, 2'–Deoxysangivamycin and Related 7–β–D–Arabinofuranosylpyrrolo[2,3–d]Pyrimidines via Ring Closure of Pyrrole Precursors Prepared by the Stereospecific Sodium Salt Glycosylation Procedure", *Tetrahedron*, vol. 42, No. 21, pp. 5869–5878, 1986.
Jendralla et al., "Efficient Kg–Scale Synthesis of Thrombin Inhibitor CRC 220", *Tetrahedron*, vol. 51, No. 44, pp. 12047–12068, 1995.

(List continued on next page.)

*Primary Examiner*—Floyd D. Higel
*Assistant Examiner*—Kamal Saeed
(74) *Attorney, Agent, or Firm*—Mary K. VanAtten

(57) ABSTRACT

The present invention relates to processes for the conversion of nitrites to amidines in the preparation of compounds which are antagonists of the platelet glycoprotein IIb/IIIa fibrinogen receptor complex. The compounds described herein are potent thrombolytics and useful for the inhibition of platelet aggregation in the treatment of thromboembolic disorders.

4 Claims, No Drawings

OTHER PUBLICATIONS

Chauhan et al., Antiparasitic Agents: Part VI Synthesis of 1,2–,1,3– & 1,4–Bis(4–substituted aryloxy)benzenes & Their Biological Activities, *Indian Journal of Chemistry*, vol. 27B, pp. 38–42, 1988.

Sindelar et al., "Synthesis of (2–(Phenylthio)Phenyl)Acetamidines and Related Amidoximes as Potential Antidepressants", *Collection Czechoslovak Chem. Commun.*, vol. 53, pp. 381–388, 1988.

Vadon et al., "Synthesis and Effects on Arginase and Nitric Oxide Synthase of Two Novel Analogues of $N^\omega$–hydroxyarginine, $N^\omega$–hydroxyindospicine and p–hydroxyamidinophenylalanine", *J. Chem. Soc., Perkin Trans. 1*, pp. 645–648, 1996.

Ram et al., "Benzylmalononitriles, a Versatile Synthon for the Synthesis of Azoles and Azines as Antimalarials", *Indian Journal of Chemistry*, vol. 33B, pp. 1048–1052, 1994.

J. David Rawn, Biochemistry, Harper & Row Pub., New York, p. 45, 1983.

Gante et al., "New Antithrombotic rgd–memetics with high bioavailability" Bioorganic and Medical Chemistry Letters, vol. 6, No. 20, 1996, p. 2425–2430.

Zhang et al, "The enantiospecific synthesis of an isoxazoline.A RGD mimic platelet GPIIb/IIIa antagonist" Journal of Organic Chemistry, vol. 8, No. 62, Apr. 18, 1997, p. 2466 (XP002077679).

Lin–Hua Zhang et al, The chiral specific synthesis of DMP 754 a platelet GPIIb/IIIa antagonist Tetrahedron Letters, vol. 26, No. 37, Jun. 24, 1996, p. 4455.

* cited by examiner

EFFICIENT METHOD FOR THE CONVERSION OF NITRILES TO AMIDINES

This application is a divisional of Ser. No. 09/346,409 filed on Jul. 1, 1999 which is a divisional of Ser. No. 09/166,722 filed on Oct. 5, 1998 now U.S. Pat. No. 5,962,693 which claims benefit of provisional application No. 60/061,707 filed on Oct. 6, 1997.

FIELD OF THE INVENTION

The present invention relates generally to processes for the conversion of cyano groups into amidines for the purpose of producing compounds which are useful as antagonists of the platelet glycoprotein IIb/IIIa fibrinogen receptor complex. These compounds may be used for the inhibition of platelet aggregation, as thrombolytics, and/or for the treatment of thromboembolic disorders.

BACKGROUND

There are several methods to convert cyano groups into amidine groups (S. Patai, Z. Rappoport, The Chemistry of Amidines and Imidates, 1991, John Wiley & Sons Ltd.). One of the most widely used methods for the preparation of amidines is the Pinner synthesis (R. Roger, D. G. Neilson, Chem. Rev. 1961, 61, 179–211), which proceeds in two steps through an imidate intermediate.

Abood et al, in U.S. Pat. No. 5,484,946, discusses formation of the amidine moiety from a nitrile group through an amidoxime intermediate. Jendrall et al, in Tetrahedron 1995, 51, 12047–12068, used a similar process to convert a cyano group into the amidinium functionality. Eloy and Leners, in Chem. Rev., 1962, 62, 155–183, review the preparation of amidoximes from nitriles. Chio and Shine, in J. Heterocyclic Chem., 1989, 26, 125–128, reported that these amidoximes can be transformed into 1,2,4-oxadiazole derivatives. Judkins et al, in Synthetic Commun. 1996, 26, 4351, describe formation of amidine moiety from nitrile through an amidoxime intermediate under acetylation or acylation conditions.

This literature however, does not disclose any regioselectivity between an amidoxime and an isoxazoline. In fact, Mueller et al, Angew. Chem., 1994, 106, 1305–1308, report that hydrogenation with 10%Pd/C will reduce a isoxazoline ring system. There is also no precedent for the transformation of a cyano group into an amidine functionality through a 1,2,4-oxadiazole moiety, and therefore the conversion of a 1,2,4-oxadiazole into amidine directly through catalytic hydrogenation is not taught.

Compounds of generic form (I) are antagonists of the platelet glycoprotein IIb/IIIa fibrinogen receptor complex which are currently being evaluated for the inhibition of platelet aggregation, as thrombolytics, and for the treatment of thromboembolic disorders. Consequently, large quantities of these compounds are needed to support drug development studies.

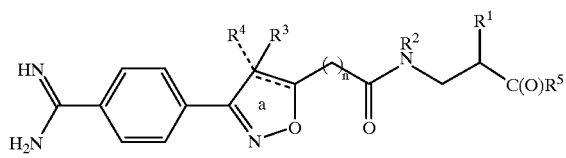

(I)

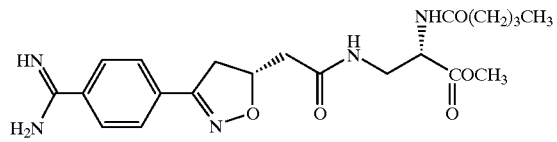

(X)

The preparation of compounds of generic form (I) have been disclosed in U.S. Pat. No. 5,446,056, PCT international publication WO 95/14683, PCT international publication WO 96/38426, pending and commonly owned U.S. application Ser. No. 08/700,906, and in J. Med. Chem., Xue et al, 1997, 40, 2064–2084. The preparation of (X) has been disclosed by Zhang et al in Tetrahedron Lett. 1996, 37, 4455–4458 and J. Org. Chem. 1997, 62, 2466–2470, which describe amidine formation from a nitrile using the Pinner reaction. Although this process has been able to produce compounds of formula (X) on a multikilogram scale, employing the Pinner reaction on a commercial scale poses several disadvantages. The Pinner approach involves the use of an excess of hydrogen chloride gas which is environmentally unfriendly, and removal of the inorganic salts generated during the Pinner process requires extensive purification protocols. It was therefore necessary to develop an efficient, safer process to produce compounds of formula (I) on large scale.

SUMMARY OF THE INVENTION

The present invention relates generally to processes for the conversion of cyano groups into amidines for the purpose of producing compounds, and intermediates therefore, which are useful as antagonists of the platelet glycoprotein IIb/IIIa fibrinogen receptor complex. These compounds may be used for the inhibition of platelet aggregation, as thrombolytics, and/or for the treatment of thromboembolic disorders.

There is provided by this invention a process for the preparation of compounds of formula (I), (III), (IV), (V) and (VI):

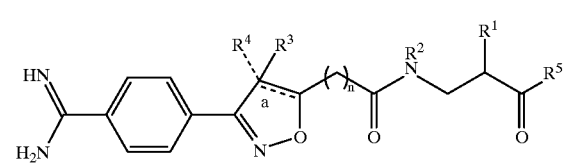

(I)

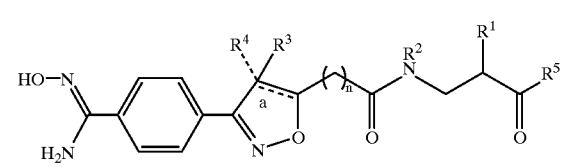

(III)

-continued

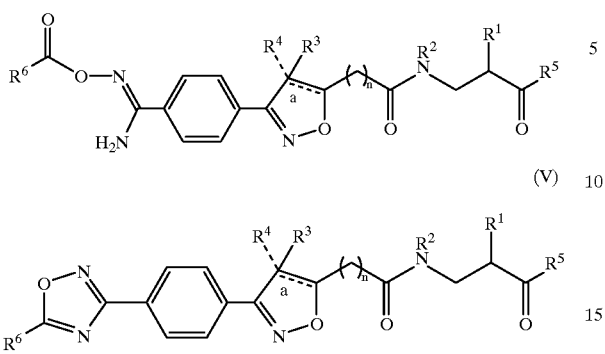

wherein:
R$^1$ is selected from H or NHR$^{1a}$;
R$^{1a}$ is selected from the group consisting of:
—C(=O)—O—R$^{1b}$,
—C(=O)—R$^{1b}$,
—C(=O)N(R$^{1b}$)$_2$,
—C(=O)NHSO$_2$R$^{1b}$,
—C(=O)NHC(=O)R$^{1b}$,
—C(=O)NHC(=O)OR$^{1b}$,
—C(=O)NHSO$_2$NHR$^{1b}$,
—C(=S)—NH—R$^{1b}$,
—NH—C(=O)—O—R$^{1b}$,
—NH—C(=O)R$^{1b}$,
—NH—C(=)—NH—R$^{1b}$,
—SO$_2$—O—R$^{1b}$,
—S$_2$—R$^{1b}$,
—SO$_2$—N(R$^{1b}$)$_2$,
—SO$_2$—NHC(=O)OR$^{1b}$,
—P(=S)(OR$^{1b}$)$_2$,
—P(=O)(OR$^{1b}$)$_2$,
—P(=S)(R$^{1b}$)$_2$,
—P(=O)(R$^{1b}$)$_2$, and

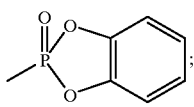

R$^{1b}$ is selected from the group consisting of:
C$_1$–C$_8$ alkyl substituted with 0-2 R$^{1c}$,
C$_2$–C$_8$ alkenyl substituted with 0-2 R$^{1c}$,
C$_2$–C$_8$ alkynyl substituted with 0-2 R$^{1c}$,
C$_3$–C$_8$ cycloalkyl substituted with 0-2 R$^{1c}$,
aryl substituted with 0-4 R$^{1c}$,
aryl(C$_1$–C$_6$ alkyl)-substituted with 0-4 R$^{1c}$,
a 5–10 membered heterocyclic ring system having 1–3 heteroatoms selected independently from O, S, and N, said heterocyclic ring being substituted with 0-4 R$^{1c}$, and
C$_1$–C$_6$ alkyl substituted with a 5–10 membered heterocyclic ring system having 1–3 heteroatoms selected independently from O, S, and N, said heterocyclic ring being substituted with 0-4R$^{1c}$;
R$^{1c}$ is H, halogen, CF$_3$, CN, NO$_2$, C–C$_8$ alkyl, C$_2$–C$_6$ alkenyl, C$_3$–C$_{11}$ cycloalkyl, C$_4$–C$_{11}$ cycloalkylalkyl, aryl, aryl(C$_1$–C$_6$ alkyl)-, C$_1$–C$_6$ alkoxy, and C$_2$–C$_5$ alkoxycarbonyl;
R$^2$ is selected from H or C$_1$–C$_{10}$ alkyl;

R$^3$ and R$^4$ are independently selected from the group consisting of H, C$_1$–C$_6$ alkyl, C$_2$–C$_6$ alkenyl, C$_2$–C$_6$ alkynyl, C$_3$–C$_7$ cycloalkyl, and aryl substituted with 0-2 R$^{3a}$;
R$^{3a}$ is selected from the group consisting of C$_1$–C$_4$ alkyl, C$_1$–C$_4$ alkoxy, halo, CF$_3$, NO$_2$, and NR$^{3b}$R$^{3c}$;
R$^{3b}$ and R$^{3c}$ are each independently selected from the group consisting of H, C$_1$–C$_{10}$ alkyl, C$_2$–C$_{10}$ alkoxycarbonyl, C$_2$–C$_{10}$ alkylcarbonyl, C$_1$–C$_{10}$ alkylsulfonyl, heteroaryl(C$_1$–C$_4$ alkyl)sulfonyl, aryl (C$_1$–C$_{10}$ alkyl)sulfonyl, arylsulfonyl, aryl, heteroarylcarbonyl, heteroarylsulfonyl, and heteroarylalkylcarbonyl, wherein said aryl and heteroaryl are optionally substituted with 0-3 R$^{3d}$;
R$^{3d}$ is selected from the group consisting of C$_1$–C$_4$ alkyl, C$_1$–C$_4$ alkoxy, halo, CF$_3$, and NO$_2$;
R$^5$ is selected from the group consisting of:
hydroxy, C$_1$–C$_{10}$ alkyloxy, C$_3$–C$_{11}$ cycloalkyloxy, C$_6$–C$_{10}$ aryloxy, C$_7$–C$_{11}$ arylalkyloxy,
C$_3$–C$_{10}$ alkylcarbonyloxyalkyloxy,
C$_3$–C$_{10}$ alkoxycarbonyloxyalkyloxy,
C$_3$–C$_{10}$ alkoxycarbonylalkyloxy,
C$_5$–C$_{10}$ cycloalkylcarbonyloxyalkyloxy,
C$_5$–C$_{10}$ cycloalkoxycarbonyloxyalkyloxy,
C$_5$–C$_{10}$ cycloalkoxycarbonylalkyloxy,
C$_8$–C$_{11}$ aryloxycarbonylalkyloxy,
C$_8$–C$_{12}$ aryloxycarbonyloxyalkyloxy,
C$_8$–C$_{12}$ arylcarbonyloxyalkyloxy,
C$_5$–C$_{10}$ alkoxyalkylcarbonyloxyalkyloxy,
5-(C$_5$–C$_{10}$ alkyl)-1,3-dioxa-cyclopenten-2-one-yl)-methyloxy,
(5-aryl-1,3-dioxa-cyclopenten-2-one-yl)-methyloxy, and
(R$^{5a}$)HN-(C$_1$–C$_{10}$ alkoxy)-;
R$^{5a}$ is selected from the group consisting of H, C$_1$–C$_4$ alkyl, aryl(C$_1$–C$_{10}$ alkoxy)carbonyl, C$_2$–C$_{10}$ alkoxycarbonyl, and C$_3$–C$_6$ alkenyl;
R$^6$ is selected from the group consisting of H, CF$_3$, CF$_2$CF$_3$, CF$_2$CF$_2$CF$_3$, CF$_2$CF$_2$CF$_2$CF$_3$, C$_1$–C$_8$ alkyl, C$_1$–C$_8$ perfluoroalkyl, C$_2$–C$_6$ alkenyl, C$_2$–C$_6$ alkynyl, C$_3$–C$_{11}$ cycloalkyl, C$_4$–C$_{11}$ cycloalkylalkyl, aryl (C$_1$–C$_6$ alkyl)-, C$_1$–C$_6$ alkoxy, C$_7$–C$_{10}$ arylalkyloxy, aryloxy and aryl substituted with 0-5 R$^{6c}$;
R$^{6c}$ is selected from the group consisting of H, halo, CF$_3$, CN, NO$_2$, NR$^{6d}$R$^{6e}$, C$_1$–C$_8$ alkyl, C$_2$–C$_6$ alkenyl, C$_3$–C$_{11}$ cycloalkyl, C$_4$–C$_{11}$ cycloalkylalkyl, aryl, aryl (C$_{1-6}$ alkyl)-, C$_1$–C$_6$ alkoxy, and C$_2$–C$_5$ alkoxycarbonyl;
R$^{6d}$ and R$^{6e}$ are independently selected from the group consisting of H, C$_1$–C$_{10}$ alkyl, C$_2$–C$_{10}$ alkoxycarbonyl, C$_2$–C$_{10}$ alkylcarbonyl, C$_1$–C$_{10}$ alkylsulfonyl, aryl, aryl (C$_1$–C$_{10}$ alkyl)sulfonyl, arylsulfonyl, heteroaryl(C$_1$–C$_4$ alkyl)sulfonyl, heteroarylcarbonyl, heteroarylsulfonyl, or heteroarylalkylcarbonyl, wherein said aryl and heteroaryl are optionally substituted with 0-3 substituents selected from the group consisting of C$_1$–C$_4$ alkyl, C$_1$–C$_4$ alkoxy, halo, CF$_3$, and NO$_2$;
n is 0–4; and
a is a single or double bond, with the proviso that if a is a double bond, it is not simultaneously substituted with R$^3$ and R$^4$;
said process comprising one or more of:
(1): contacting a compound of formula (II) with a salt of hydroxyl amine in the presence of a suitable base to form a compound of formula (III);

(2): contacting a compound of formula (III) with an acylating agent of formula $R^6CO—O—COR^6$ or $R^6COX$, wherein X is fluorine, bromine, chlorine or imidazole, in a suitable solvent to form a compound of formula (IV) or a salt thereof; and (3): contacting a compound of formula (IV) with hydrogen under a suitable pressure in the presence of a hydrogenation catalyst to form a compound of formula (I) or a pharmaceutically acceptable salt form thereof.

DETAILED DESCRIPTION OF THE INVENTION

In a first embodiment, the present invention provides a process for the preparation of compounds of formula (I):

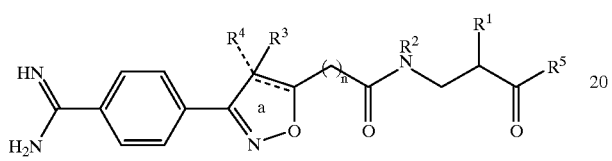

(I)

or a pharmaceutically acceptable salt form thereof; wherein:

$R^1$ is selected from H or $NHR^{1a}$;

$R^{1a}$ is selected from the group consisting of:
—C(=O)—O—$R^{1b}$,
—C(=O)—$R^{1b}$,
—C(=O)N($R^{1b}$)$_2$,
—C(=O)NHSO$_2R^{1b}$,
—C(=O)NHC(=O)$R^{1b}$,
—C(=O)NHC(=O)O$R^{1b}$,
—C(=O)NHSO$_2$NH$R^{1b}$,
—C(=S)—NH—$R^{1b}$,
—NH—C(=O)—O—$R^{1b}$,
—NH—C(=O)$R^{1b}$,
—NH—C(=)—NH—$R^{1b}$,
—SO$_2$—O—$R^{1b}$,
—SO$_2$—$R^{1b}$,
—SO$_2$—N($R^{1b}$)$_2$,
—SO$_2$—NHC(=O)O$R^{1b}$,
—P(=S)(O$R^{1b}$)$_2$,
—P(=O)(O$R^{1b}$)$_2$,
—P(=S)($R^{1b}$)$_2$,
—P(=O)($R^{1b}$)$_2$, and

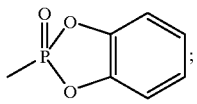

$R^{1b}$ is selected from the group consisting of:
$C_1$–$C_8$ alkyl substituted with 0-2 $R^{1c}$,
$C_2$–$C_8$ alkenyl substituted with 0-2 $R^{1c}$,
$C_2$–$C_8$ alkynyl substituted with 0-2 $R^{1c}$,
$C_3$–$C_8$ cycloalkyl substituted with 0-2 $R^{1c}$,
aryl substituted with 0-4 $R^{1c}$,
aryl($C_1$–$C_6$ alkyl)-substituted with 0-4 $R^{1c}$,
a 5–10 membered heterocyclic ring system having 1–3 heteroatoms selected independently from O, S, and N, said hetero cyclic ring being substituted with 0-4 $R^{1c}$, and
$C_1$–$C_6$ alkyl substituted with a 5–10 membered heterocyclic ring system having 1–3 heteroatoms selected independently from O, S, and N, said heterocyclic ring being substituted with 0-4$R^{1c}$;

$R^{1c}$ is H, halogen, $CF_3$, CN, $NO_2$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy, and $C_2$–$C_5$ alkoxycarbonyl;

$R^2$ is selected from H or $C_1$–$C_{10}$ alkyl;

$R^3$ and $R^4$ are independently selected from the group consisting of H, $C_1$–$C_6$ alkyl, $C_2$–$C_6$ alkenyl, $C_2$–$C_6$ alkynyl, $C_3$–$C_7$ cycloalkyl, and aryl substituted with 0-2 $R^{3a}$;

$R^{3a}$ is selected from the group consisting of $C_1$–$C_4$ alkyl, $C_1$–$C_4$ alkoxy, halo, $CF_3$, $NO_2$, and $NR^{3b}R^{3c}$;

$R^{3b}$ and $R^{3c}$ are each independently selected from the group consisting of H, $C_1$–$C_{10}$ alkyl, $C_2$–$C_{10}$ alkoxycarbonyl, $C_2$–$C_{10}$ alkylcarbonyl, $C_1$–$C_{10}$ alkylsulfonyl, heteroaryl($C_1$–$C_4$ alkyl)sulfonyl, aryl ($C_1$–$C_{10}$ alkyl)sulfonyl, arylsulfonyl, aryl, heteroarylcarbonyl, heteroarylsulfonyl, and heteroarylalkylcarbonyl, wherein said aryl and heteroaryl are optionally substituted with 0-3 $R^{3d}$;

$R^{3d}$ is selected from the group consisting of $C_1$–$C_4$ alkyl, $C_1$–$C_4$ alkoxy, halo, $CF_3$, and $NO_2$;

$R^5$ is selected from the group consisting of:
hydroxy, $C_1$–$C_{10}$ alkyloxy, $C_3$–$C_{11}$ cycloalkyloxy,
$C_6$–$C_{10}$ aryloxy, $C_7$–$C_{11}$ arylalkyloxy,
$C_3$–$C_{10}$ alkylcarbonyloxyalkyloxy,
$C_3$–$C_{10}$ alkoxycarbonyloxyalkyloxy,
$C_3$–$C_{10}$ alkoxycarbonylalkyloxy,
$C_5$–$C_{10}$ cycloalkylcarbonyloxyalkyloxy,
$C_5$–$C_{10}$ cycloalkoxycarbonyloxyalkyloxy,
$C_5$–$C_{10}$ cycloalkoxycarbonylalkyloxy,
$C_8$–$C_{11}$ aryloxycarbonylalkyloxy,
$C_8$–$C_{12}$ aryloxycarbonyloxyalkyloxy,
$C_8$–$C_{12}$ arylcarbonyloxyalkyloxy,
$C_5$–$C_{10}$ alkoxyalkylcarbonyloxyalkyloxy,
5-($C_5$–$C_{10}$ alkyl)-1,3-dioxa-cyclopenten-2-one-yl)-methyloxy,
(5-aryl-1,3-dioxa-cyclopenten-2-one-yl)-methyloxy, and
($R^5$a)HN-($C_1$–$C_{10}$ alkoxy)-;

$R^{5a}$ is selected from the group consisting of H, $C_1$–$C_4$ alkyl, aryl($C_1$–$C_{10}$ alkoxy)carbonyl, $C_2$–$C_{10}$ alkoxycarbonyl, and $C_3$–$C_6$ alkenyl;

n is 0–4;

a is a single or double bond, with the proviso that if a is a double bond, it is not simultaneously substituted with $R^3$ and $R^4$;

said process comprising:
contacting a compound of formula (IV):

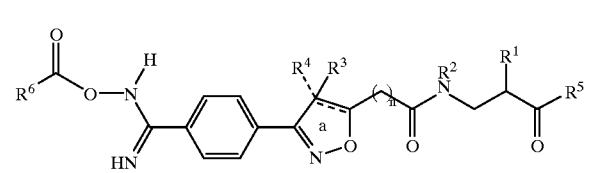

(IV)

wherein:

$R^6$ is selected from the group consisting of H, $CF_3$, $CF_2CF_3$, $CF_2CF_2CF_3$, $CF_2CF_2CF_2CF_3$, $C_1$–$C_8$ alkyl, $C_1$–$C_8$ perfluoroalkyl, $C_2$–$C_6$ alkenyl, $C_2$–$C_8$ alkynyl, $C_3$–$C_{11}$ cycloalkyl, $C_4$–$C_{11}$ cycloalkylalkyl, aryl ($C_1$–$C_6$ alkyl)-, $C_1$–$C_6$ alkoxy, $C_7$–$C_{10}$ arylalkyloxy, $C_1$–$C_6$ alkyloxy, aryloxy and aryl substituted with 0-5 $R^{6c}$;

$R^{6c}$ is selected from the group consisting of H, halo, $CF_3$, CN, $NO_2$, $NR^{6d}R^{6e}$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl ($C_1$–$C_6$ alkyl)-, $C_1$–$C_6$ alkoxy, and $C_2$–$C_5$ alkoxycarbonyl;

$R^{6d}$ and $R^{6e}$ are independently selected from the group consisting of H, $C_1$–$C_{10}$ alkyl, $C_2$–$C_{10}$ alkoxycarbonyl, $C_2$–$C_{10}$ alkylcarbonyl, $C_1$–$C_{10}$ alkylsulfonyl, aryl, aryl ($C_1$–$C_{10}$ alkyl)sulfonyl, arylsulfonyl, heteroaryl($C_1$–$C_4$ alkyl)sulfonyl, heteroarylcarbonyl, heteroarylsulfonyl, or heteroarylalkylcarbonyl, wherein said aryl and heteroaryl are optionally substituted with 0-3 substituents selected from the group consisting of $C_1$–$C_4$ alkyl, $C_1$–$C_4$ alkoxy, halo, $CF_3$, and $NO_2$;

with hydrogen under a suitable pressure in the presence of a hydrogenation catalyst to form a compound of formula (I) or a pharmaceutically acceptable salt form thereof.

In a preferred embodiment, the present invention provides a process for the preparation of a compound of formula (I), wherein:
said suitable pressure is up to 100 psi, and
said hydrogenation catalyst is selected from the group consisting of palladium on carbon, palladium hydroxide on carbon, palladium on calcium carbonate and platinum on carbon.

In a more preferred embodiment, the present invention provides a process for the preparation of a compound of formula (I), wherein:

$R^1$ is selected from H or $NHR^{1a}$;
$R^{1a}$ is —C(=O)—O—$R^{1b}$ or —$SO_2$—$R^{1b}$;
$R^1b$ is selected from the group consisting of:
  $C_1$–$C_8$ alkyl substituted with 0-1 $R^{1c}$,
  $C_2$–$C_8$ alkenyl substituted with 0-1 $R^{1c}$,
  $C_2$–$C_8$ alkynyl substituted with 0-1 $R^{1c}$,
  $C_3$–$C_8$ cycloalkyl substituted with 0-1 $R^{1c}$,
  aryl substituted with 0-3 $R^{1c}$,
  aryl($C_1$–$C_6$ alkyl)-substituted with 0-3 $R^{1c}$,
  a 5–10 membered heterocyclic ring system having 1–3 heteroatoms selected independently from O, S, and N, said heterocyclic ring being substituted with 0-4 $R^{1c}$, and
  $C_1$–$C_6$ alkyl substituted with a 5–10 membered heterocyclic ring system having 1–3 heteroatoms selected independently from O, S, and N, said heterocyclic ring being substituted with 0-4 $R^{1c}$;

$R^{1c}$ is selected from the group consisting of H, halogen, $CF_3$, CN, $NO_2$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy and $C_2$–$C_5$ alkoxycarbonyl;

$R^2$ is H or $C_1$–$C_{10}$ alkyl;
$R^3$ and $R^4$ are H or $C_1$–$C_6$ alkyl;
$R^5$ is selected from the group consisting of hydroxy, $C_1$–$C_{10}$ alkyloxy, $C_3$–$C_{11}$ cycloalkyloxy, $C_6$–$C_{10}$ aryloxy and $C_7$–$C_{11}$ arylalkyloxy;

$R^6$ is selected from the group consisting of H, $C_1$–$C_6$ alkyl, $C_2$–$C_6$ alkenyl, $C_2$–$C_6$ alkynyl, $C_3$–$C_7$ cycloalkyl, $C_1$–$C_8$ perfluoroalkyl, $C_7$–$C_{10}$ arylalkyloxy, $C_1$–$C_6$ alkyloxy, aryloxy, aryl substituted with 0-2 $R^{6c}$;

$R^{6c}$ is H, halogen, $CF_3$, CN, $NO_2$, $NR^{6d}R^{6e}$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy, and $C_2$–$C_5$ alkoxycarbonyl; and $R^{6d}$ and $R^{6e}$ are independently selected from H or $C_1$–$C_{10}$ alkyl;
n is 1;
a is a single or double bond, with the proviso that if a is a double bond, it is not simultaneously substituted with $R^3$ and $R^4$.

In an even more preferred embodiment, the present invention provides a process for the preparation of a compound of formula (I-a):

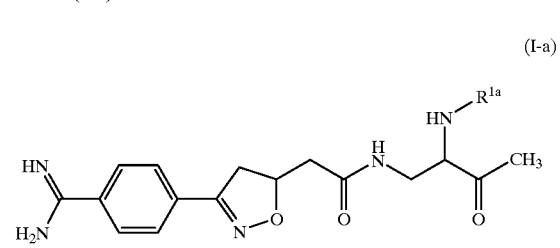

(I-a)

or a pharmaceutically acceptable salt form thereof, wherein:
$R^{1a}$ is —C(=O)O$CH_2$($CH_2$)$_2$$CH_3$ or 3,5-dimethyloxazol-4-yl-sulfonyl;
comprising contacting a compound of formula (IV-a):

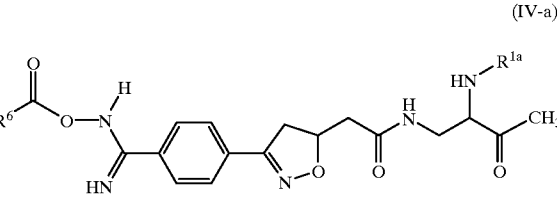

(IV-a)

wherein $R^6$ is H, methyl, ethyl, propyl, butyl, pentyl, hexyl $C_7$–$C_8$ arylalkyloxy, $C_1$–$C_5$ alkyloxy, aryloxy or aryl;
with hydrogen under a suitable pressure from about 20 to about 50 psi in the presence of palladium on carbon, in the range of about 1% to about 10% by weight of compound (IV), to form a compound of formula (I) or a pharmaceutically acceptable salt form thereof.

In a second embodiment, the present invention provides a process for the preparation of compounds of formula (IV) or a salt thereof comprising:
contacting a compound of formula (III):

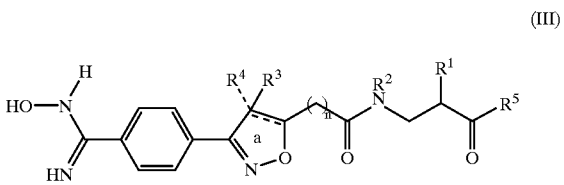

(III)

with an acylating agent of formula $R^6CO$—O—$COR^6$ or $R^6COX$, wherein X is fluorine, bromine, chlorine or imidazole, in a suitable solvent to form a compound of formula (IV) or a salt thereof.

In a preferred second embodiment, the present invention provides a process for the preparation of a compound of formula (IV), wherein:
X is chlorine;
$R^1$ is $NHR^{1a}$;
$R^{1a}$ is —C(=O)O$CH_2$($CH_2$)$_2$$CH_3$ or 3,5-dimethyloxazol-4-yl-sulfonyl;
$R^2$ is H;

$R^3$ and $R^4$ are H;
$R^5$ is methyl;
$R^6$ is $CH_3$;
n is 1;
a is a single bond; and
said suitable solvent is acetic acid.

In a third embodiment, the present invention provides a process for the preparation of compounds of formula (III), comprising:
contacting a compound of formula (II):

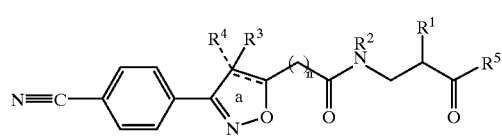

(II)

with a salt of hydroxyl amine in the presence of a suitable base to form a compound of formula (III).

In a preferred third embodiment, the present invention provides a process for the preparation of a compound of formula (III), wherein said salts of hydroxyl amine are hydroxylamine hydrochloride and hydroxlyamine sulfate.

In a more preferred third embodiment, the present invention provides a process for the preparation of a compound of formula (III), wherein:

X is chlorine;
$R^1$ is $NHR^{1a}$;
$R^{1a}$ is $-C(=O)-O-CH_2(CH_2)_2CH_3$ or 3,5-dimethyloxazol-4yl-sulfonyl;
$R^2$ is H;
$R^3$ and $R^4$ are H;
$R^5$ is methyl;
$R^6$ is selected from the group consisting of:
    H, $C_1-C_6$ alkyl, $C_7-C_8$ arylalkyloxy, $C_1-C_5$ alkyloxy, aryloxy and aryl;
n is 1;
a is a single bond;
said suitable salt of hydroxylamine is hydroxlyamine hydrochloride; and
the suitable base is selected from the group consisting of: triethylamine, diisopropylethylamine and 4-methyl morpholine.

In a fourth embodiment, the present invention provides a process for the preparation of compounds of formula (I):

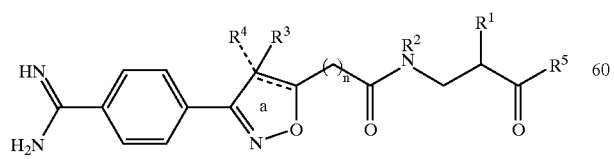

(I)

or a pharmaceutically acceptable salt form thereof,
said process comprising:

(a) heating a compound of the formula (IV):

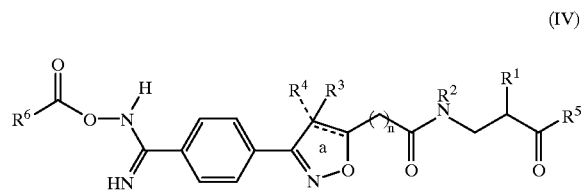

(IV)

wherein:
$R^1$ is selected from H or $NHR^{1a}$;
$R^{1a}$ is selected from the group consisting of:
    $-C(=O)-O-R^{1b}$,
    $-C(=O)-R^{1b}$,
    $-C(=O)N(R^{1b})_2$,
    $-C(=O)NHSO_2R^{1b}$,
    $-C(=O)NHC(=O)R^{1b}$,
    $-C(=O)NHC(=O)OR^{1b}$,
    $-C(=O)NHSO_2NHR^{1b}$,
    $-C(=S)-NH-R^{1b}$,
    $-NH-C(=O)-O-R^{1b}$,
    $-NH-C(=O)R^{1b}$,
    $-NH-C(=)-NH-R^{1b}$,
    $-SO_2O-R^{1b}$,
    $-SO_2-R^{1b}$,
    $-SO_2N(R^{1b})_2$,
    $-SO_2-NHC(=O)OR^{1b}$,
    $-P(=S)(OR^{1b})_2$,
    $-P(=O)(OR^{1b})_2$,
    $-P(=S)(R^{1b})_2$,
    $-P(=O)(R^{1b})_2$, and

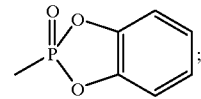;

$R^{1b}$ is selected from the group consisting of:
    $C_1-C_8$ alkyl substituted with 0-2 $R^{1c}$,
    $C_2-C_8$ alkenyl substituted with 0-2 $R^{1c}$,
    $C_2-C_8$ alkynyl substituted with 0-2 $R^{1c}$,
    $C_3-C_8$ cycloalkyl substituted with 0-2 $R^{1c}$,
    aryl substituted with 0-4 $R^{1c}$,
    aryl($C_1-C_6$ alkyl)-substituted with 0-4 $R^{1c}$,
    a 5–10 membered heterocyclic ring system having 1–3 heteroatoms selected independently from O, S, and N, said heterocyclic ring being substituted with 0-4 $R^{1c}$, and
    $C_1-C_6$ alkyl substituted with a 5–10 membered heterocyclic ring system having 1–3 heteroatoms selected independently from O, S, and N, said heterocyclic ring being substituted with 0-4$R^{1c}$;
$R^{1c}$ is H, halogen, $CF_3$, CN, $NO_2$, $C_1-C_8$ alkyl, $C_2-C_6$ alkenyl, $C_3-C_{11}$ cycloalkyl, $C_4-C_{11}$ cycloalkylalkyl, aryl, aryl($C_1-C_6$ alkyl)-, $C_1-C_6$ alkoxy, and $C_2-C_5$ alkoxycarbonyl;
$R^2$ is selected from H or $C_1-C_{10}$ alkyl;
$R^3$ and $R^4$ are independently selected from the group consisting of H, $C_1-C_6$ alkyl, $C_2-C_6$ alkenyl, $C_2-C_6$ alkynyl, $C_3-C_7$ cycloalkyl, and aryl substituted with 0-2 $R^{3a}$;
$R^{3a}$ is selected from the group consisting of $C_1-C_4$ alkyl, $C_1-C_4$ alkoxy, halo, $CF_3$, $NO_2$, and $NR^{3b}R^{3c}$;
$R^{3b}$ and $R^{3c}$ are each independently selected from the group consisting of H, $C_1-C_{10}$ alkyl, $C_2-C_{10}$ alkoxycarbonyl, $C_2$–$C_{10}$ alkylcarbonyl, $C_1$–$C_{10}$ alkylsulfonyl, heteroaryl($C_1$–$C_4$ alkyl)sulfonyl, aryl ($C_1$–$C_{10}$ alkyl)sulfonyl, arylsulfonyl, aryl, heteroarylcarbonyl, heteroarylsulfonyl, and heteroarylalkylcarbonyl, wherein said aryl and heteroaryl are optionally substituted with 0-3 $R^{3d}$;

$R^{3d}$ is selected from the group consisting of $C_1$–$C_4$ alkyl, $C_1$–$C_4$ alkoxy, halo, $CF_3$, and $NO_2$;

$R^5$ is selected from the group consisting of:
hydroxy, $C_1$–$C_{10}$ alkyloxy, $C_3$–$C_{11}$ cycloalkyloxy,
$C_6$–$C_{10}$ aryloxy, $C_7$–$C_{11}$ arylalkyloxy,
$C_3$–$C_{10}$ alkylcarbonyloxyalkyloxy,
$C_3$–$C_{10}$ alkoxycarbonyloxyalkyloxy,
$C_3$–$C_{10}$ alkoxycarbonylalkyloxy,
$C_5$–$C_{10}$ cycloalkylcarbonyloxyalkyloxy,
$C_5$–$C_{10}$ cycloalkoxycarbonyloxyalkyloxy,
$C_5$–$C_{10}$ cycloalkoxycarbonylalkyloxy,
$C_8$–$C_{11}$ aryloxycarbonylalkyloxy,
$C_8$–$C_{12}$ aryloxycarbonyloxyalkyloxy,
$C_8$–$C_{12}$ arylcarbonyloxyalkyloxy,
$C_5$–$C_{10}$ alkoxyalkylcarbonyloxyalkyloxy,
5-($C_5$–$C_{10}$ alkyl)-1,3-dioxa-cyclopenten-2-one-yl)-methyloxy,
(5-aryl-1,3-dioxa-cyclopenten-2-one-yl)-methyloxy, and
($R^{5a}$)HN-($C_1$–$C_{10}$ alkoxy)-;

$R^{5a}$ is selected from the group consisting of H, $C_1$–$C_4$ alkyl, aryl($C_1$–$C_{10}$ alkoxy)carbonyl, $C_2$–$C_{10}$ alkoxycarbonyl, and $C_3$–$C_6$ alkenyl;

$R^6$ is selected from the group consisting of H, $CF_3$, $CF_2CF_3$, $CF_2CF_2CF_3$, $CF_2CF_2CF_2CF_3$, $C_1$–$C_8$ alkyl, $C_1$–$C_8$ perfluoroalkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl($C_1$–$C_6$ alkyl)-, $C_1$–$C_6$ alkoxy, $C_7$–$C_{10}$ arylalkyloxy, aryloxy and aryl substituted with 0-5 $R^{6c}$;

$R^{6c}$ is selected from the group consisting of H, halo, $CF_3$, CN, $NO_2$, $NR^{6d}R^{6e}$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl ($C_1$–$C_6$ alkyl)-, $C_1$–$C_6$ alkoxy, and $C_2$–$C_5$ alkoxycarbonyl;

$R^{6d}$ and $R^{6e}$ are independently selected from the group consisting of H, $C_1$–$C_{10}$ alkyl, $C_2$–$C_{10}$ alkoxycarbonyl, $C_2$–$C_{10}$ alkylcarbonyl, $C_1$–$C_{10}$ alkylsulfonyl, aryl, aryl ($C_1$–$C_{10}$ alkyl)sulfonyl, arylsulfonyl, heteroaryl($C_1$–$C_4$ alkyl)sulfonyl, heteroarylcarbonyl, heteroarylsulfonyl, or heteroarylalkylcarbonyl, wherein said aryl and heteroaryl are optionally substituted with 0-3 substituents selected from the group consisting of $C_1$–$C_4$ alkyl, $C_1$–$C_4$ alkoxy, halo, $CF_3$, and $NO_2$;

n is 0–4;

a is a single or double bond, with the proviso that if a is a double bond, it is not simultaneously substituted with $R^3$ and $R^4$;

for a time sufficient, and to a temperature sufficient to form a compound of formula (V):

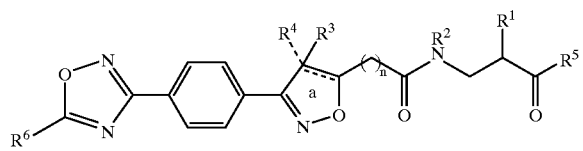

(V)

and (b) contacting said compound of formula (V) with hydrogen under a suitable pressure in the presence of a hydrogenation catalyst to form a compound of formula (I) or a salt thereof.

In a preferred fourth embodiment, the present invention provides a process for the preparation of a compound of formula (I), wherein:

said suitable pressure is up to 100 psi;

said hydrogenation catalyst is selected from the group consisting of palladium on carbon, palladium hydroxide on carbon, palladium on calcium carbonate and platinum on carbon;

said sufficient temperature is from about 30° C. to about 120° C.;

said sufficient time is from about 10 minutes to about 24 hours;

wherein an amount of catalyst loaded on carbon is from about 1% to about 10% by weight; and wherein an amount of a hydrogenation catalyst is from about 1% to about 30% by weight of compound (IV).

In a more preferred fourth embodiment, the present invention provides a process for the preparation of a compound of formula (I), wherein:

$R^1$ is $NHR^{1a}$;

$R^{1a}$ is —C(=O)—O—$CH_2(CH_2)_2CH_3$ or 3,5-dimethyloxazol-4yl-sulfonyl;

$R^2$ is H;

$R^3$ and $R^4$ are H;

$R^5$ is methyl;

$R^6$ is selected from the group consisting of:
H, methyl, ethyl, propyl, butyl, pentyl, hexyl, $C_7$–$C_8$ arylalkyloxy, aryloxy, $C_1$–$C_5$ alkoxy and aryl;

n is 1, and a is a single bond;

said suitable pressure is from about 20 to about 50 psi;

said sufficient temperature is from about 50° C. to about 120° C.;

said sufficient time is from about 10 minutes to about 3 hours;

said hydrogenation catalyst is palladium on carbon;

wherein an amount of catalyst loaded on carbon is from about 3% to about 5% by weight; and wherein an amount of palladium on carbon is from about 3% to about 7% by weight of compound (IV).

In a fifth embodiment, the present invention provides a process for the preparation of compounds of the formula (I):

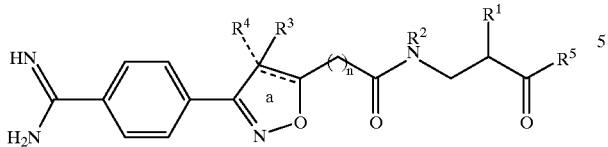
(I)

or a pharmaceutically acceptable salt form thereof;
wherein:
$R^1$ is selected from H or $NHR^{1a}$;
$R^{1a}$ is selected from the group consisting of:
—C(=O)—O—$R^{1b}$,
—C(=O)—$R^{1b}$,
—C(=O)N($R^{1b}$)$_2$,
—C(=O)NHSO$_2$$R^{1b}$,
—C(=O)NHC(=O)$R^{1b}$,
—C(=O)NHC(=O)O$R^{1b}$,
—C(=O)NHSO$_2$NH$R^{1b}$,
—C(=S)—NH—$R^{1b}$,
—NH—C(=O)—O—$R^{1b}$,
—NH—C(=O)$R^{1b}$,
—NH—C(=)—NH—$R^{1b}$,
—SO$_2$—$R^{1b}$,
—SO$_2$—N($R^{1b}$)$_2$,
—SO$_2$—NHC(=O)O$R^{1b}$,
—P(=S)(O$R^{1b}$)$_2$,
—P(=O)(O$R^{1b}$)$_2$,
—P(=S)($R^{1b}$)$_2$,
—P(=O)($R^{1b}$)$_2$, and

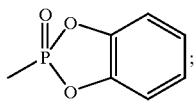

$R^{1b}$ is selected from the group consisting of:
$C_1$–$C_8$ alkyl substituted with 0-2 $R^{1c}$,
$C_2$–$C_8$ alkenyl substituted with 0-2 $R^{1c}$,
$C_2$–$C_8$ alkynyl substituted with 0-2 $R^{1c}$,
$C_3$–$C_8$ cycloalkyl substituted with 0-2 $R^{1c}$,
aryl substituted with 0-4 $R^{1c}$,
aryl($C_1$–$C_6$ alkyl)-substituted with 0-4 $R^{1c}$,
a 5–10 membered heterocyclic ring system having 1–3 heteroatoms selected independently from O, S, and N, said heterocyclic ring being substituted with 0-4 $R^{1c}$, and
$C_1$–$C_6$ alkyl substituted with a 5–10 membered heterocyclic ring system having 1–3 heteroatoms selected independently from O, S, and N, said heterocyclic ring being substituted with 0-4$R^{1c}$;
$R^{1c}$ is H, halogen, $CF_3$, CN, $NO_2$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$alkyl)-, $C_1$–$C_6$ alkoxy, and $C_2$–$C_5$ alkoxycarbonyl;
$R^2$ is selected from H or $C_1$–$C_{10}$ alkyl;
$R^3$ and $R^4$ are independently selected from the group consisting of H, $C_1$–$C_6$ alkyl, $C_2$–$C_6$ alkenyl, $C_2$–$C_6$ alkynyl, $C_3$–$C_7$ cycloalkyl, and aryl substituted with 0-2 $R^{3a}$;
$R^{3a}$ is selected from the group consisting of $C_1$–$C_4$ alkyl, $C_1$–$C_4$ alkoxy, halo, $CF_3$, $NO_2$, and $NR^{3b}R^{3c}$;
$R^{3b}$ and $R^{3c}$ are each independently selected from the group consisting of H, $C_1$–$C_{10}$ alkyl, $C_2$–$C_{10}$ alkoxycarbonyl, $C_2$–$C_{10}$ alkylcarbonyl, $C_1$–$C_{10}$ alkylsulfonyl, heteroaryl($C_1$–$C_4$ alkyl)sulfonyl, aryl ($C_1$–$C_{10}$ alkyl) sulfonyl, arylsulfonyl, aryl, heteroarylcarbonyl, heteroarylsulfonyl, and heteroarylalkylcarbonyl, wherein said aryl and heteroaryl are optionally substituted with 0-3 $R^{3d}$;
$R^{3d}$ is selected from the group consisting of $C_1$–$C_4$ alkyl, $C_1$–$C_4$ alkoxy, halo, $CF_3$, and $NO_2$;
$R^5$ is selected from the group consisting of:
hydroxy, $C_1$–$C_{10}$ alkyloxy, $C_3$–$C_{11}$ cycloalkyloxy, $C_6$–$C_{10}$ aryloxy, $C_7$–$C_{11}$ arylalkyloxy, $C_3$–$C_{10}$ alkylcarbonyloxyalkyloxy, $C_3$–$C_{10}$ alkoxycarbonyloxyalkyloxy, $C_3$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_8$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, 5-($C_5$–$C_{10}$ alkyl)-1,3-dioxa-cyclopenten-2-one-yl)-methyloxy, (5-aryl-1,3-dioxa-cyclopenten-2-one-yl)-methyloxy, and
($R^{5a}$)HN—($C_1$–$C_{10}$ alkoxy)-;
$R^{5a}$ is selected from the group consisting of H, $C_1$–$C_4$ alkyl, aryl($C_1$–$C_{10}$ alkoxy)carbonyl, $C_2$–$C_{10}$ alkoxycarbonyl, and $C_3$–$C_6$ alkenyl;
n is 0–4;
a is a single or double bond, with the proviso that if a is a double bond, it is not simultaneously substituted with $R^3$ and $R^4$;
said process comprising:
contacting a compound of formula (VI):

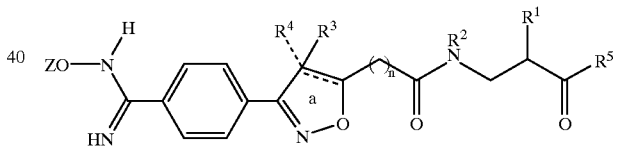

(VI)

wherein:
Z is selected from $R^6SO_2$— or ($R^7$)$_3$Si—;
$R^6$ is selected from the group consisting of H, $CF_3$, $CF_2CF_3$, $CF_2CF_2CF_3$, $CF_2CF_2CF_2CF_3$, $C_1$–$C_8$ alkyl, $C_1$–$C_8$ perfluoroalkyl, $C_2$–$C_6$ alkenyl, $C_2$–$C_6$ alkynyl, $C_3$–$C_{11}$ cycloalkyl, $C_4$–$C_{11}$ cycloalkylalkyl, aryl ($C_1$–$C_6$ alkyl)-, $C_1$–$C_6$ alkoxy, $C_7$–$C_{10}$ arylalkyloxy, aryloxy and aryl substituted with 0-5 $R^{6c}$;
$R^{6c}$ is selected from the group consisting of H, halo, $CF_3$, CN, $NO_2$, $NR^{6d}R^{6e}$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl ($C_1$–$C_6$ alkyl)-, $C_1$–$C_6$ alkoxy, and $C_2$–$C_5$ alkoxycarbonyl;
$R^{6d}$ and $R^{6e}$ are independently selected from the group consisting of H, $C_1$–$C_{10}$ alkyl, $C_2$–$C_{10}$ alkoxycarbonyl, $C_2$–$C_{10}$ alkylcarbonyl, $C_1$–$C_{10}$ alkylsulfonyl, aryl, aryl ($C_1$–$C_{10}$ alkyl)sulfonyl, arylsulfonyl, heteroaryl($C_1$–$C_4$ alkyl)sulfonyl, heteroarylcarbonyl, heteroarylsulfonyl, or heteroarylalkylcarbonyl, wherein said aryl and heteroaryl are optionally substituted with 0-3 substituents selected from the group consisting of $C_1$–$C_4$ alkyl, $C_1$–$C_4$ alkoxy, halo, $CF_3$, and $NO_2$;

$R^7$ is selected independently from $C_1$–$C_{10}$ alkyl or aryl substituted 0-3 $R^{7a}$; and $R^{7a}$ is $C_1$–$C_{10}$ alkyl;

with hydrogen under a suitable pressure in the presence of a hydrogenation catalyst to form a compound of formula (I) or a pharmaceutically acceptable salt form thereof.

In a sixth embodiment, the present invention provides a process for the preparation of compounds of formula (VI):

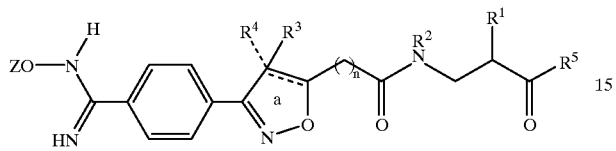

(VI)

comprising: contacting a compound of formula (III):

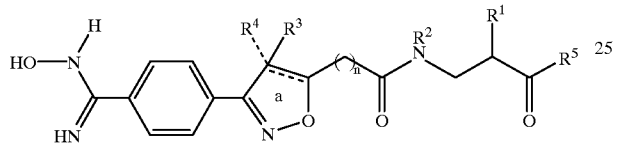

(III)

with an agent of formula Z-X, wherein:

X is fluorine, bromine or chlorine;

Z is $R^6SO_2$— or $(R^7)_3Si$—;

$R^7$ is selected independently from $C_1$–$C_{10}$ alkyl or aryl substituted 0-3 $R^{7a}$; and $R^{7a}$ is $C_1$–$C_{10}$ alkyl;

in the presence of a suitable acid scavenger in a suitable solvent to form a compound of formula (IV) or a salt thereof.

In a seventh embodiment, the present invention provides a compound of formula (III-i):

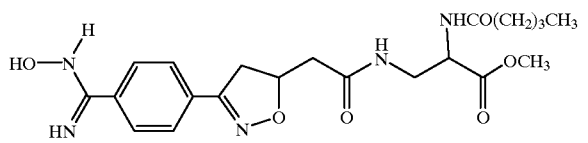

(III-i)

and salt forms thereof.

In a eighth embodiment, the present invention provides a compound of formula (IV-i):

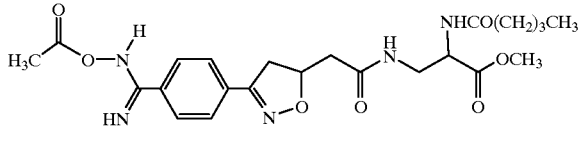

(IV-i)

and salt forms thereof.

In a ninth embodiment, the present invention provides a compound of formula (V-i):

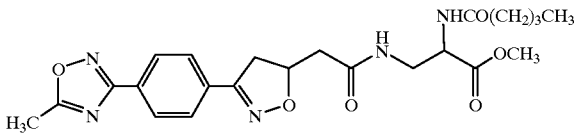

(V-i)

and salt forms thereof.

DEFINITIONS

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

Suitable halogenated solvents include: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include: benzene, cyclohexane, pentane, hexane, toluene, cycloheptane, methylcyclohexane, heptane, ethylbenzene, m-, o-, or p-xylene, octane, indane, nonane, or naphthalene.

Suitable carboxylic acid solvents include acetic acid, trifluoroacetic acid, ethanoic acid, propionic acid, propiolic acid, butyric acid, 2-butynoic acid, vinyl acetic acid, pentanoic acid, hexanoic acid, heptanoic acid, octanoic acid, nonanoic acid and decanoic acid.

Suitable pressures range from atmospheric to any pressure obtainable in a laboratory or industrial plant.

Suitable hydrogenation catalysts are those which facilitate the delivery of hydrogen to the N—O bond of an N-acylated hydroxylamine. Such hydrogenation catalysts by way of example and without limitation are palladium on carbon, palladium hydroxide on carbon, palladium on calcium carbonate poisoned with lead and platinum on carbon.

As used herein, suitable acid scavengers include those compounds capable of accepting a proton from a hydroxyamidine during either an acylation, sulfonation or silation reaction without reacting with the agent reacting with the oxygen of the hydroxyamidine. Examples include, but are not limited to tertiary bases such as N,N-diisopropylethylamine, 2,3-, 2,4-, 2,5-, 2,6-, 3,4-, 3,5-lutidine, triethylamine, 2-, 3-, or 4-picoline, pyrrole, pyrrolidine, N-methyl morpholine, pyridine and pyrimidine.

As used herein, suitable bases include those soluble in the reaction solvent and capable of free-basing hydroxylamine. Examples include, but are not limited to: lithium hydroxide, sodium hydroxide, potassium hydroxide, lithium carbonate, sodium carbonate, potassium carbonate, imidazole, ethylene diamine, N,N-diisopropylethylamine, 2,3-, 2,4-, 2,5-, 2,6-, 3,4-, 3,5-lutidine, triethylamine, 2-, 3-, or 4-picoline, pyrrole, pyrrolidine, N-methyl morpholine, pyridine, pyrimidine or piperidine.

As used herein, acylating agent refers to an acid halide or anhydride, which, when reacted with a hydroxyamidine results in O-acylation of the hydroxyl amidine. Such acylating agents by way of example and without limitation are of the general structure $R^6COX$ or $R^6CO—O—COR^6$, as defined above in the specification. By way of further example, and without limitation, where X is fluorine, chlorine, bromine or imidazole, $R^6$ is H, $CF_3$, $CF_2CF_3$, $CF_2CF_2CF_3$, $CF_2CF_2CF_2CF_3$, methyl, ethyl, propyl, butyl, ethenyl, allyl, ethynyl, cyclopropyl, phenyl, benzyl, $C_7–C_{10}$ arylalkyloxy, $C_1–C_{10}$ alkyloxy or aryloxy.

As used herein, agent refers to a compound of the formula Z-X, which, when reacted with a hydroxyamidine results in placement of the Z group on the oxygen of the hydroxyamidine. By way of further example, and without limitation, where X is fluorine, chlorine, bromine or imidazole, Z is either $R^6SO_2$— or $(R^7)_3Si$—, $R^6$ is H, $CF_3$, $CF_2CF_3$, $CF_2CF_2CF_3$, $CF_2CF_2CF_2CF_3$, methyl, ethyl, propyl, butyl, ethenyl, allyl, ethynyl, cyclopropyl, phenyl, benzyl, $C_7–C_{10}$ arylalkyloxy, or aryloxy, and $R^7$ is independently selected from $C_1–C_{10}$ alkyl or aryl substituted with 0-3 $R^{7a}$, and $R^{7a}$ is $C_1–C_{10}$ alkyl.

The compounds described herein may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. Methods on how to prepare optically active forms from optically active starting materials are known in the art, such as by resolution of racemic forms or by synthesis. All chiral, diastereomeric, racemic forms and all geometric isomeric forms of a structure are intended.

When any variable (for example but not limited to $R^{1b}$, $R^{1c}$, $R^{3a}$, $R^{3b}$, $R^{3c}$, $R^{6c}$, etc.) occurs more than one time in any constituent or in any formula, its definition on each occurrence is independent of its definition at every other occurrence. Thus, for example, if a group is shown to be substituted with 0-2 $R^{3a}$, then said group may optionally be substituted with up to two $R^{3a}$ and $R^{3a}$ at each occurrence is selected independently from the defined list of possible $R^{3a}$.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound.

As used herein, "alkyl" is intended to include both branched and straight-chain saturated aliphatic hydrocarbon groups having the specified number of carbon atoms; for example, $C_1–C_4$ alkyl includes methyl, ethyl, n-propyl, i-propyl, n-butyl, i-butyl, s-butyl, and t-butyl; for example $C_1–C_{10}$ alkyl includes $C_1–C_4$ alkyl, pentyl, hexyl, heptyl, octyl, nonyl, decyl, and isomer thereof.

As used herein, any carbon range such as "$C_x–C_y$," is intended to mean a minimum of "x" carbons and a maximum of "y" carbons representing the total number of carbons in the substituent to which it refers. For example, "$C_3–C_{10}$ alkylcarbonyloxyalkyloxy" could contain one carbon for "alkyl", one carbon for "carbonyloxy" and one carbon for "alkyloxy" giving a total of three carbons, or a larger number of carbons for each alkyl group not to exceed a total of ten carbons.

"Alkenyl" is intended to include hydrocarbon chains of either a straight or branched configuration and one or more unsaturated carbon-carbon bonds which may occur in any stable point along the chain, such as ethenyl, 1-propenyl, 2-propenyl, 1-butenyl, 2-butenyl, 3-butenyl, 1,3-butadienyl and the like. "Alkynyl" is intended to include hydrocarbon chains of either a straight or branched configuration and one or more triple carbon-carbon bonds which may occur in any stable point along the chain, such as ethynyl, propynyl, butynyl and the like. "Aryl" is intended to mean phenyl or naphthyl. The term "arylalkyl" represents an aryl group attached through an alkyl bridge; for example aryl($C_1–C_2$) alkyl is intended to mean benzyl, phenylethyl and the like.

As used herin, "cycloalkyl" is intended to include saturated ring groups, including mono-, bi-, or poly-cyclic ring systems, such as cyclopropyl, cyclobutyl, cyclopentyl, cyclohexyl, cycloheptyl, cyclooctyl, and adamantyl.

As used herein, "alkyloxy" or "alkoxy" represents an alkyl group of indicated number of carbon atoms attached through an oxygen bridge, for example methoxy, ethoxy, propoxy, i-propoxy, butoxy, i-butoxy, s-butoxy and t-butoxy. The term "aryloxy" is intended to mean phenyl or naphthyl attached through an oxygen bridge;

As used herein, "carbonyl" means a carbon double bonded to oxygen and additionally substituted with two groups through single bonds; "carbonyloxy" means a carbon double bonded to oxygen and additionally bonded through a single bonds to two groups, one of which is an oxygen. As used herein, "sulfonyl" is intended to mean a sulfur bonded through double bonds to two oxygens and bonded to two additional groups through single bonds. As used herein, "hydroxy" means a group consisting of an oxygen and a hydrogen bonded to another group through the oxygen.

"Halo" or "halogen" as used herein refers to fluoro, chloro, bromo and iodo.

As used herein, the term "heterocycle" or "heterocyclic" is intended to mean a stable 5- to 10-membered monocyclic or bicyclic or 5- to 10-membered bicyclic heterocyclic ring which may be saturated, partially unsaturated, or aromatic, and which consists of carbon atoms and from 1 to 3 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolyl, oxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocylic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyridazinyl, benzofuranyl, benzothienyl, benzimidazolyl, quinolinyl, or isoquinolinyl.

As used herein, "pharmaceutically acceptable salts" refer to derivatives of the disclosed compounds wherein the intermediates or final compound are modified by making acid or base salts of the intermediates or final compounds. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the intermediates or final compounds include the conventional inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts are generally prepared by reacting the free base or acid with stoichiometric amounts or with an excess of the desired salt-forming inorganic or organic acid or base in a suitable solvent or various combinations of solvents.

The pharmaceutically acceptable salts of the acids of the intermediates or final compounds are prepared by combination with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference. The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention, by way of example and without limitation, may be further understood by reference to Scheme 1. Scheme 1 details the general synthetic method for synthesis of compounds of formula (I). Compound (II) can be prepared by methods described in *J. Org. Chem.* 1997, 62, 2466–2470, and *Tetrahedron Lett.* 1996, 37, 4455–4458. It is understood to one skilled in the art that the anhydride or acid chlorides used in the acylation step can be prepared by conversion of carboxylic acid derivatives as described in *Advanced Organic Chemistry, March,* 4th edition, John Wiley and Sons, Inc., 1992, p. 401–402 and p. 437–438.

SCHEME 1

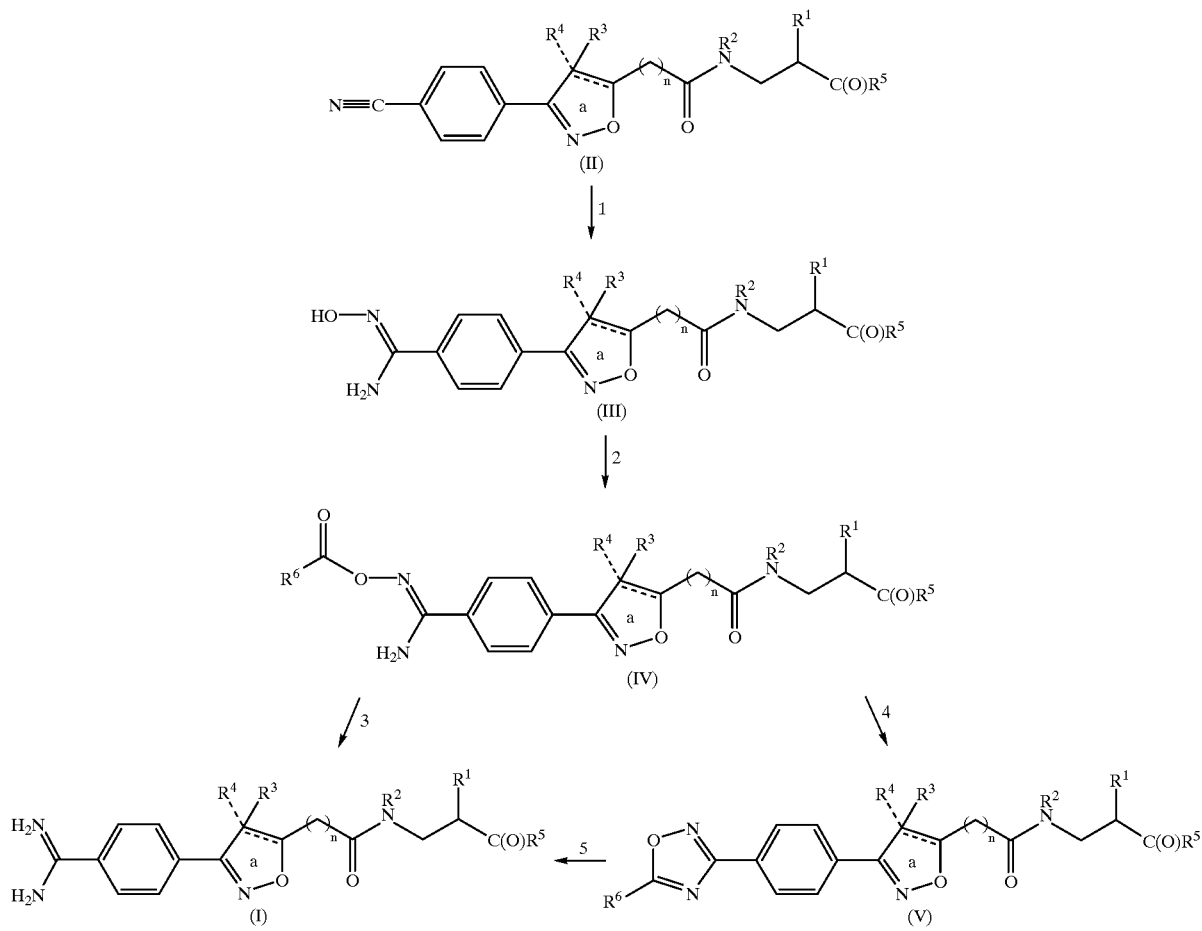

In reaction 1, a compound of formula (II) is dissolved in about 10 liters of suitable solvent per kilogram of compound (II). A suitable salt of hydroxyl amine is added. While a wide range of solvents such as halogenated, protic, aprotic, hydrocarbon, or ethers can be used, protic solvents such as methanol, ethanol and isopropanol are preferred, of which methanol is most preferred. Suitable salts of hydroxyl amine include phosphate, sulfate, nitrate and hydrochloride salts; a most preferred salt is hydroxyl amine hydrochloride. The hydroxyl amine salt is free-based with about 1.0 to about 2.0 equivalents of an appropriate base. Preferrable bases are tertiary amines; most preferred is triethyl amine. The reaction mixture can then be heated for a time sufficent to form a compound of form (III). By way of general guidance, compound (II) may be contacted with free-based hydroxyl amine at about 40° C. to about 65° C. for about 1 to about 5 hours to produce compound (III). Preferred temperatures are from about 55° C. to about 65° C. Preferred reaction times are from about 2 to about 4 hours. The product precipitates as a white solid during the course of the reaction. The solids can then be filtered and the cake washed with a solvent, the choice of which is readily understood by one skilled in the art. The product is dried to afford pure compound (III).

In reaction 2, a vessel is charged with compound (III). The solids are dissolved in a suitable solvent followed by the slow charging of the vessel with a second solution made by dissolving a suitable acylating agent in the solvent being used for the reaction. Preferably, the addition of the acylating agent solution should be done over a period of about 15 minutes to about one hour. While a wide range of reaction solvents such as halogenated, aprotic, hydrocarbon, ether, or organic acids are possible, preferred solvents are acetic acid, trifluoroacetic acid, pyridine, chloroform, dichloromethane, dichlorobenzene, acetonitrile, and tetrahydrofuran. Most preferred are carboxylic acids which are structural derivatives of the acylating agent being used. By way of general example, acetic acid would preferably be used as the solvent when acetic anhydride is the acylating agent, whereas triflouroacetic acid would be preferably used when trifluoroacetic anhydride is the acylating agent. Certain solvents such as aprotic, ether, halogenated and hydrocarbon solvents may require the addition of an acid scavenger. Preferred acid scavengers include tertiary bases such as triethyl amine, diisopropyl ethylamine, N-methyl morpholine and pyridine. Most preferred is triethyl amine. Solvents capable of reacting with the acylating agent, such as alcohols, water and the like are not preferred as is readily understood by one skilled in the art. Preferred acylating agents are anhydrides. Most preferred is acetic anhydride. Further, the acylating agent (and preferable solvent) can be strategically chosen to form the desired salt of the reaction product. By way of general example, acetic anhydride would be selected as the acylating agent if the acetate salt of the product is desired. The choice of acylating agent and solvent in this regard is readily understood by one skilled in the art.

After the addition of the acylating agent, the reaction progression can be monitored by HPLC analysis performed on an aliquot of the reaction solution. The acylation reaction is considered finished when compound (III) is completely consumed. Typical reaction times are in the range of about 5 minutes to about 24 hours. Preferred reaction times are about 5 minutes to about 3 hours. The product can be isolated by the removal of the solvent via distillation and precipitation of the product through the addition of a suitable aprotic solvent. Preferred aprotic solvents are ethers. The choice of precipition solvent and the methods of isolation are readily understood by one skilled in the art. Preferably, the product is carried forward without isolation.

Reaction 3, comprises the hydrogenation of the O-substituted hydroxyamidine. This reaction can be carried out without isolation of compound (IV), by the addition of a slurry of a suitable hydrogention catalyst in the solvent used in the preceding reaction. If compound (IV) is isolated, the hydrogenation can be carried out in protic, aprotic, hydrocarbon, ether, or organic acid solvents. The preferred solvents are methanol, ethanol, 2-propanol, dimethylformamide, ethyl acetate, anisole, acetic acid and trifluoroacetic acid. Most preferred is a mixture of methanol and acetic acid. While numerous hydrogenation catalysts are possible, palladium on carbon is most preferred. The amount of catalyst loaded on the carbon ranges from about 0.5% to about 30%. The preferred amount of catalyst on carbon is about 1% to about 10%. Most preferred is about 3% to 5%. The total weight of the catalyst and carbon per gram of starting material is preferably about 1% to about 10%. Most preferred is about 3% to 7%. The total weight of catalyst and carbon is based on the weight of the O-alkylated hydroxyamidine. The reaction solution is then subjected to a hydrogen atmosphere under a suitable pressure. Preferred pressures range from about 1 psi to 100 psi. Most preferred is 20 psi to 50 psi. The reaction time of the hydrogenation is dependent on cumulative factors, including the amount of catalyst present, the reaction temperature and the hydrogen pressure. By way of general example, an acetylation reaction containing 10.0 kilograms of compound (III) required the use of 0.5 kilograms of 3% palladium on carbon, under 5 psi of hydrogen at room temperature to reach completion in about 5 hours. Varying any one of these conditions will effect reaction time which is readily understood by one skilled in the art.

Reaction completion can be monitored by HPLC analysis performed on aliquots of the reaction mixture. The reaction is considered complete when compound (IV) has been completely consumed. After the reaction is judged complete, the catalyst is filtered off and washed with reaction solvent. The filtrate is concentrated, and the product precipitated by the addition of a suitable aprotic solvent. The most preferred solvent for precipitation is acetone. The choice of precipition solvent and the methods of isolation are readily understood by one skilled in the art. The product is then filtered and dried to give pure compound (I).

In reaction 4, the resultant reaction solution of Step 2 is heated to form compound (V). The heating range is from about 30° C. to the reflux temperature of the solvent. Preferred temperatures are from about 30° C. to about 120° C. Preferred solvents for the cyclization are acetic acid, trifluoroacetic acid, pyridine, chloroform, dichloromethane, dichlorobenzene, acetonitrile, and tetrahydrofuran. The most preferred solvent for the cyclization is acetic acid. The preferred time of reflux is solvent dependent due to the limitations of boiling points. By way of general example, the use of acetic acid as the solvent required a heating time of about 3 hours. The product can be isolated by the removal of the solvent via distillation followed by the drying of the solids. Preferably, compound (V) is carried forward without isolation.

In reaction 4, compound (V) is hydrogenated under the identical conditions of Reaction 3 to give compound (I). The present invention may be further exemplified without limitation by reference to Scheme 2.

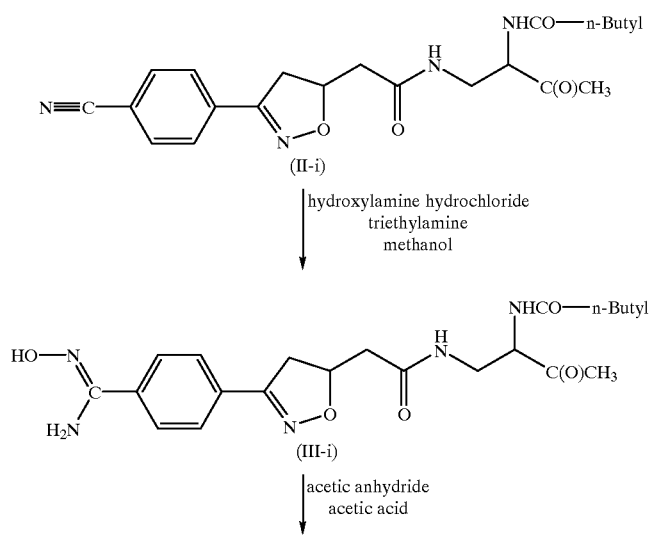

SCHEME 2

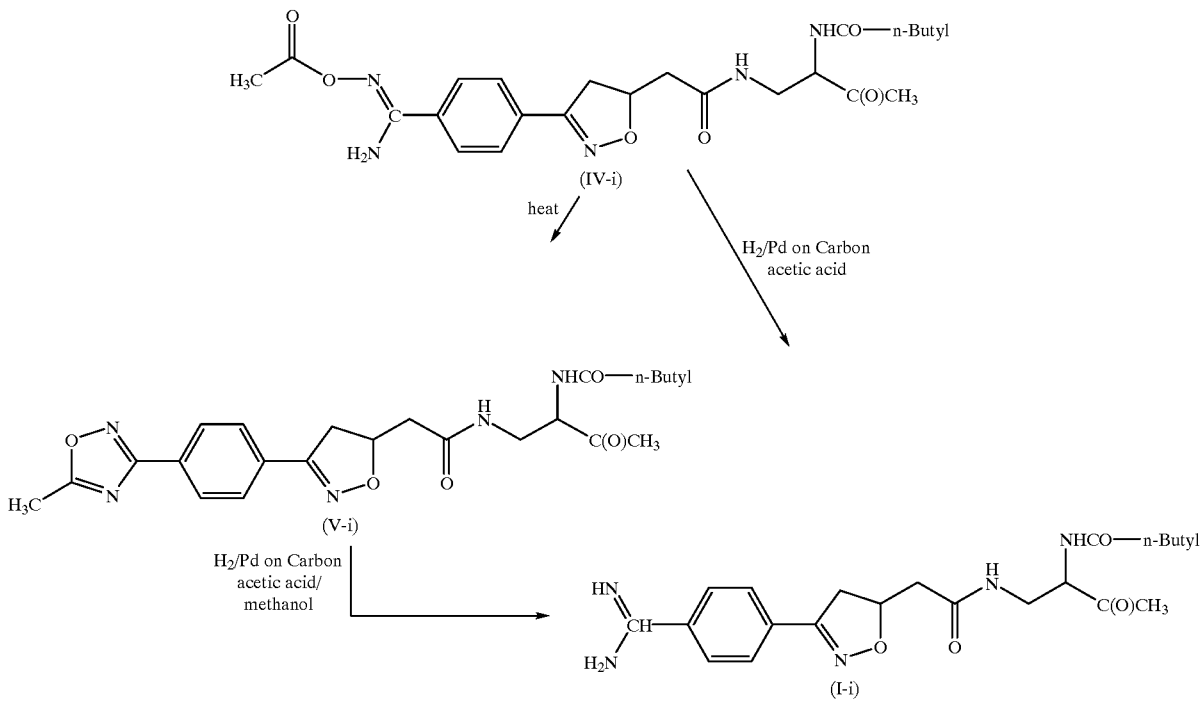

The following examples are meant to be illustrative of the present invention. These examples are presented to exemplify the invention and are not to be construed as limiting the inventors scope.

EXAMPLE 1
(R)-Methyl-3-[[[3[4[amino(hydroxyimino)methyl]phenyl]-4,5-dihydro-5-isoxazolyl]acetyl]amino]-N (butoxy-carbonyl)-L-alanine: Compound (III-i)

A 100 gal stainless steel reactor was charged with methanol (87 Kg), compound (II-i) (11 Kg), hydroxylamine hydrochloride (3.6 Kg), and triethylamine (5.2 Kg). The reaction mixture was heated at 60° C. for 3 h and a large amount of solid precipitated during the reaction. After cooling to 0–5° C., the solid was filtered through a Nutsche filter and the cake was washed with a mixture of methanol and water (made from 20 Kg of methanol and 25 Kg of water). After dried the cake, the product (11.8 Kg) was obtained.

EXAMPLE 2
(R)-Methyl-3-[[[3-[4-(aminoiminomethyl)phenyl]-4,5-dihydro-5-isoxazolyl]acetyl]amino]-N(butoxy carbonyl)-L-alanine monoacetate: Compound (I-i)

A 50 gal stainless steel reactor was charged with acetic acid(63 Kg) and (R)-Methyl-3[[[3[4[amino(hydroxyimino) methyl]phenyl]-4,5-dihydro-5-isoxazolyl]acetyl]amino]-N (butoxy-carbonyl)-L-alanine (Batch 1: 10.0 Kg; Batch 2: 10.0 Kg.) A solution of acetic anhydride (Batch 1: 2205 g; Batch 2: 1983 g) in acetic acid (21 Kg) was charged into the reactor slowly over 30 min from a pressure cylinder using nitrogen pressure at rt (22° C.). Additional 5.3 Kg of acetic acid was then used to rinse the cylinder. After stirring at 22° C. for 30 min or until a clear solution was attained, a small sample was taken for HPLC analysis. After the reaction was complete as determined by HPLC. A slurry of Pd/C (Batch 1: 3%Pd/C, 0.5 Kg; Batch 2: 5%Pd/C, 0.4 Kg) in acetic acid (5 L) was added and the resulting mixture was hydrogenated under 5 psi hydrogen pressure for 4–5 h. After the reaction was complete as determined by HPLC, the catalyst was filtered off and washed with acetic acid (21 Kg) to give a solution of the product. Anisole (80 Kg) was then added to the filtrate and the resulting mixture was concentrated at about 70° C. under vacuum (40 mm Hg or lower) in a 100 gal reactor. The distillation was stopped until that the distillate was about 148 L or the solid became visible in the batch. Cooled the reactor to 40° C., 72 Kg of acetone was added over 30–90 min. The slurry was stirred at ambient temperature for 1 h and the 0–5° C. for another 1 h. The solid was collected on a Rosenmund filter/dryer and the cake was washed with 10% methanol in acetone (made from 6 Kg of methanol and 57 Kg of acetone). The solid cake was dried until LOD<1%. A hot (80° C.) mixture of acetonitrile (27 Kg) and acetic acid (18 Kg) was charged into the filter to dissolve the cake and the hot solution was then transfer back to 100 gal reactor. The transfer line was washed with a mixture of acetic acid (0.9 Kg) and acetonitrile (1.4 Kg). After the solution was cooled to 40–45° C., acetone (65 Kg) was added within 10 min. The resulting slurry was stirred gently at 25° C. for 1 h and then 0–5° C. for another 1 h. The solid was filtered by the Rosenmund filter/dryer and the cake was washed with 10% methanol in acetone (prepared from 5.5 Kg methanol and 50 Kg of acetone). After drying the cake until LOD<0.1%, the product was obtained (Batch 1: 6.3 Kg. Batch 2: 6.8 Kg). Heels from both batches in the Rosenmund filter/dryer were dissolved in acetonitrile and acetic acid and combined, which was crystallized in the Kilo lab to give additional 2.86 Kg of product.

EXAMPLE 3
(R)-methyl-3-[[[3-[4-[(acetyloxyimino)aminomethyl] phenyl]-4,5-dihydro-5-isoxazolyl]acetyl]amino]-N-(butoxycarbonyl)-L-alanine: Compound (IV-i)

To a suspension of (R)-Methyl-3-[[[3-[4-[amino (hydroxyimino)methyl]phenyl]-4,5-dihydro-5-isoxazolyl] acetyl]amino]-N-(butoxycarbonyl)-L-alanine (11.76 g) in acetic acid (50 mL) was added acetic anhydride (3.6 g)

dropwise. After the completion of addition, the reaction mixture was stirred at room temperature 15 min. The reaction mass became clear. Ether (200 mL) was added slowly and a thick slurry formed. The resulting mixture was then stirred for another 1.5 h at room temperature and the solid was filtered. The cake was washed with ether (50 mL) and dried to give (R)-methyl-3-[[[3-[4-[(acetyloxyimino) aminomethyl] phenyl]-4,5-dihydro-5-isoxazolyl]acetyl] amino]-N-(butoxycarbonyl)-L-alanine (12.3 g).

EXAMPLE 4

(R)-methyl-N-(butoxycarbonyl)-3-[[[4,5-dihydro-3-[4-(5-methyl-1,2,4-oxadiazol-3-yl)phenyl]-5-isoxazolyl]acetyl] amino]-L-alanine: Compound (V-i)

To a suspension of (R)-Methyl-3-[[[3-[4-[amino (hydroxyimino)methyl]phenyl]-4,5-dihydro-5-isoxazolyl] acetyl]amino]-N-(butoxycarbonyl)-L-alanine (1.05 g) in acetic acid (7 mL) was added acetic anhydride (0.35 g) dropwise. After the completion of addition, the reaction mixture was refluxed for 3 h. The solvent was distilled under vacuum and the solid was dried to give (R)-methyl-N-(butoxycarbonyl)-3-[[[4,5-dihydro-3-[4-(5-methyl-1,2,4-oxadiazol-3-yl)phenyl]-5-isoxazolyl]acetyl]amino]-L-alanine (1.05 g).

EXAMPLE 5

(R)-Methyl-3-[[[3-[4-(aminoiminomethyl)phenyl]-4,5-dihydro-5-isoxazolyl]acetyl]amino]-N-(butoxy-carbonyl)-L-alanine monoacetate: Compound (I-i) Method B:

A mixture of (R)-methyl-N-(butoxycarbonyl)-3-[[[4,5-dihydro-3-[4-(5-methyl-1,2,4-oxadiazol-3-yl)phenyl]-5-isoxazolyl]acetyl]amino]-L-alanine (70 mg) and 3%Pd/C (30 mg) in methanol (3 mL) and acetic acid (0.5 mL) was stirred under hydrogen atmosphere for 3 h. The catalyst was filtered off and washed with methanol (4 mL). The combined filtrate and wash was concentrated to small volume. Acetone (2 mL) was added slowly and a slurry was formed. After stirred for 30 min, the solid was filtered and the cake was washed with 10% methanol in acetone (4 mL) and dried to give the product (25 mg).

| HPLC CONDITIONS | |
|---|---|
| Column: | Eclipse XDB-C8 4.6 × 250 mm |
| Mobile Phase: | A: 0.1% trifluoroacetic acid/0.1% triethylamine in HPLC grade water B: tetrahydrofuran (unstabilized-suitable for liquid chromatography)/0.1% trifluoroacetic acid |
| Gradient: | t = 0 min 85% A 15% B t = 10 min 85% A 15% B t = 32 min 50% A 50% B t = 40 min 50% A 50% B |
| Flow Rate: | 1.5 mL/min |
| Injection Volume: | 10 microliters |
| Stop Time: | 40 minutes |
| Post Time: | 10 minutes |
| Oven Temp.: | 40° C. |
| Detector: | UV (280 nm, 230 nm, 260 nm) |

Sample Prep.: Dissolve approximately 0.5 mg of sample (dry solids weight) per mL in 50% tetrahydrofuran 49.9% H₂0/0.1% acetic acid. Filter any undissolved solids through an Acrodisc 0.45 micron Nylon filter.

What is claimed is:
1. A process for the preparation of compound (I)

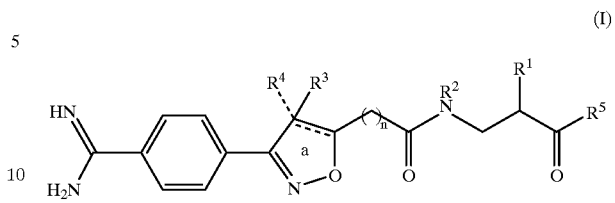

(I)

or a pharmaceutically acceptable salt form thereof, said process comprising:
(a) heating a compound of the formula (IV):

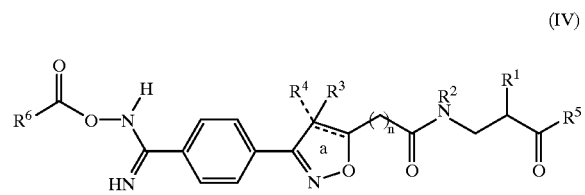

(IV)

wherein:
$R^1$ is selected from H or $NHR^{1a}$;
$R^{1a}$ is selected from the group consisting of:
—C(=O)—O—$R^{1b}$,
—C(=O)—$R^{1b}$,
—C(=O)N($R^{1b}$)$_2$,
—C(=O)NHSO$_2$$R^{1b}$,
—C(=O)NHC(=O)$R^{1b}$,
—C(=O)NHC(=O)O$R^{1b}$,
—C(=O)NHSO$_2$NH$R^{1b}$,
—C(=S)—NH—$R^{1b}$,
—NH—C(=O)—O—$R^{1b}$,
—NH—C(=O)$R^{1b}$,
—NH—C(=)—NH—$R^{1b}$,
—SO$_2$—O—$R^{1b}$,
—SO$_2$—$R^{1b}$,
—SO$_2$—N($R^{1b}$)$_2$,
—SO$_2$—NHC(=O)O$R^{1b}$,
—P(=S)(O$R^{1b}$)$_2$,
—P(=O)(O$R^{1b}$)$_2$,
—P(=S)($R^1$b)$_2$,
—P(=O)($R^{1b}$)$_2$, and

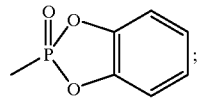
;

$R^{1b}$ is selected from the group consisting of:
$C_1$–$C_8$ alkyl substituted with 0-2 $R^{1c}$,
$C_2$–$C_8$ alkenyl substituted with 0-2 $R^{1c}$,
$C_2$–$C_8$ alkynyl substituted with 0-2 $R^{1c}$,
$C_3$–$C_8$ cycloalkyl substituted with 0-2 $R^{1c}$,
aryl substituted with 0-4 $R^{1c}$,
aryl($C_1$–$C_6$ alkyl)-substituted with 0-4 $R^{1c}$,
a 5–10 membered heterocyclic ring system having 1–3 heteroatoms selected independently from O, S, and N, said heterocyclic ring being substituted with 0-4 $R^{1c}$, and
$C_1$–$C_6$ alkyl substituted with a 5–10 membered heterocyclic ring system having 1–3 heteroatoms selected independently from O, S, and N, said heterocyclic ring being substituted with 0-4$R^{1c}$;

$R^{1c}$ is H, halogen, $CF_3$, CN, $NO_2$, $C_1$-$C_8$ alkyl, $C_2$-$C_6$ alkenyl, $C_3$-$C_{11}$ cycloalkyl, $C_4$-$C_{11}$ cycloalkylalkyl, aryl, aryl($C_1$-$C_6$ alkyl)-, $C_1$-$C_6$ alkoxy, and $C_2$-$C_5$ alkoxycarbonyl;

$R^2$ is selected from H or $C_1$-$C_{10}$ alkyl;

$R^3$ and $R^4$ are independently selected from the group consisting of H, $C_1$-$C_6$ alkyl, $C_2$-$C_6$ alkenyl, $C_2$-$C_6$ alkynyl, $C_3$-$C_7$ cycloalkyl, and aryl substituted with 0-2 $R^{3a}$;

$R^{3a}$ is selected from the group consisting of $C_1$-$C_4$ alkyl, $C_1$-$C_4$ alkoxy, halo, $CF_3$, $NO_2$, and $NR^{3b}R^{3c}$;

$R^{3b}$ and $R^{3c}$ are each independently selected from the group consisting of H, $C_1$-$C_{10}$ alkyl, $C_2$-$C_{10}$ alkoxycarbonyl, $C_2$-$C_{10}$ alkylcarbonyl, $C_1$-$C_{10}$ alkylsulfonyl, heteroaryl($C_1$-$C_4$ alkyl)sulfonyl, aryl ($C_1$-$C_{10}$ alkyl)sulfonyl, arylsulfonyl, aryl, heteroarylcarbonyl, heteroarylsulfonyl, and heteroarylalkylcarbonyl, wherein said aryl and heteroaryl are optionally substituted with 0-3 $R^{3d}$;

$R^{3d}$ is selected from the group consisting of $C_1$-$C_4$ alkyl, $C_1$-$C_4$ alkoxy, halo, $CF_3$, and $NO_2$;

$R^5$ is selected from the group consisting of:
hydroxy, $C_1$-$C_{10}$ alkyloxy, $C_3$-$C_{11}$ cycloalkyloxy, $C_6$-$C_{10}$ aryloxy, $C_7$-$C_{11}$ arylalkyloxy,
$C_3$-$C_{10}$ alkylcarbonyloxyalkyloxy,
$C_3$-$C_{10}$ alkoxycarbonyloxyalkyloxy,
$C_3$-$C_{10}$ alkoxycarbonylalkyloxy,
$C_5$-$C_{10}$ cycloalkylcarbonyloxyalkyloxy,
$C_5$-$C_{10}$ cycloalkoxycarbonyloxyalkyloxy,
$C_5$-$C_{10}$ cycloalkoxycarbonylalkyloxy,
$C_8$-$C_{11}$ aryloxycarbonylalkyloxy,
$C_8$-$C_{12}$ aryloxycarbonyloxyalkyloxy,
$C_8$-$C_{12}$ arylcarbonyloxyalkyloxy,
$C_5$-$C_{10}$ alkoxyalkylcarbonyloxyalkyloxy,
5-($C_5$-$C_{10}$ alkyl)-1,3-dioxa-cyclopenten-2-one-yl)-methyloxy,
(5-aryl-1,3dioxa-cyclopenten-2-one-yl)-methyloxy, and
($R^{5a}$)HN—($C_1$-$C_{10}$ alkoxy)-;

$R^{5a}$ is selected from the group consisting of H, $C_1$-$C_4$ alkyl, aryl($C_1$-$C_{10}$ alkoxy)carbonyl, $C_2$-$C_{10}$ alkoxycarbonyl, and $C_3$-$C_6$ alkenyl;

$R^6$ is selected from the group consisting of H, $CF_3$, $CF_2CF_3$, $CF_2CF_2CF_3$, $CF_2CF_2CF_2CF_3$, $C_1$-$C_8$ alkyl, $C_1$-$C_8$ perfluoroalkyl, $C_2$-$C_6$ alkenyl, $C_2$-$C_6$ alkynyl, $C_3$-$C_{11}$ cycloalkyl, $C_4$-$C_{11}$ cycloalkylalkyl, aryl ($C_1$-$C_6$ alkyl)-, $C_1$-$C_6$ alkoxy, $C_7$-$C_{10}$ arylalkyloxy, aryloxy and aryl substituted with 0-5 $R^{6c}$;

$R^{6c}$ is selected from the group consisting of H, halo, $CF_3$, CN, $NO_2$, $NR^{6d}R^{6e}$, $C_1$-$C_8$ alkyl, $C_2$-$C_6$ alkenyl, $C_3$-$C_{11}$ cycloalkyl, $C_4$-$C_{11}$ cycloalkylalkyl, aryl, aryl ($C_1$-$C_6$ alkyl)-, $C_1$-$C_6$ alkoxy, and $C_2$-$C_5$ alkoxycarbonyl;

$R^{6d}$ and $R^{6e}$ are independently selected from the group consisting of H, $C_1$-$C_{10}$ alkyl, $C_2$-$C_{10}$ alkoxycarbonyl, $C_2$-$C_{10}$ alkylcarbonyl, $C_1$-$C_{10}$ alkylsulfonyl, aryl, aryl ($C_1$-$C_{10}$ alkyl)sulfonyl, arylsulfonyl, heteroaryl($C_1$-$C_4$ alkyl)sulfonyl, heteroarylcarbonyl, heteroarylsulfonyl, or heteroarylalkylcarbonyl, wherein said aryl and heteroaryl are optionally substituted with 0-3 substituents selected from the group consisting of $C_1$-$C_4$ alkyl, $C_1$-$C_4$ alkoxy, halo, $CF_3$, and $NO_2$;

n is 0-4;

a is a single or double bond, with the proviso that if a is a double bond, it is not simultaneously substituted with $R^3$ and $R^4$;

for a time sufficient, and to a temperature sufficient to form a compound of formula (V):

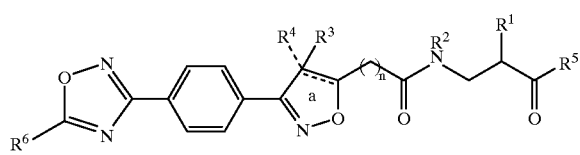

(V)

and;

(b) reacting said compound of formula (V) with hydrogen under a suitable pressure in the presence of a hydrogenation catalyst to form a compound of formula (I) or a salt thereof.

2. The process of claim 1, wherein:

said suitable pressure is up to 100 psi;

said hydrogenation catalyst is selected from the group consisting of palladium on carbon, palladium hydroxide on carbon, palladium on calcium carbonate and platinum on carbon;

said sufficient temperature is from about 30° C. to about 120° C.;

said sufficient time is from about 10 minutes to about 24 hours;

wherein an amount of catalyst loaded on carbon is from about 1% to about 10% by weight; and wherein an amount of a hydrogenation catalyst is from about 1% to about 30% by weight of compound (IV).

3. The process of claim 1, wherein:

$R^1$ is selected from H or $NHR^{1a}$;

$R^{1a}$ is —C(=O)—O—$R^{1b}$ or —$SO_2$—$R^{1b}$;

$R^{1b}$ is selected from the group consisting of:
$C_1$-$C_8$ alkyl substituted with 0-1 $R^{1c}$,
$C_2$-$C_8$ alkenyl substituted with 0-1 $R^{1c}$,
$C_2$-$C_8$ alkynyl substituted with 0-1 $R^{1c}$,
$C_3$-$C_8$ cycloalkyl substituted with 0-1 $R^{1c}$,
aryl substituted with 0-3 $R^{1c}$,
aryl($C_1$-$C_6$ alkyl)-substituted with 0-3 $R^{1c}$,
a 5-10 membered heterocyclic ring system having 1-3 heteroatoms selected independently from O, S, and N, said heterocyclic ring being substituted with 0-4 $R^{1c}$, and
$C_1$-$C_6$ alkyl substituted with a 5-10 membered heterocyclic ring system having 1-3 heteroatoms selected independently from O, S and N, said heterocyclic ring being substituted with 0-4 $R^{1c}$;

$R^{1c}$ is selected from the group consisting of H, halogen, $CF_3$, CN, $NO_2$, $C_1$-$C_8$ alkyl, $C_2$-$C_6$ alkenyl, $C_3$-$C_{11}$ cycloalkyl, $C_4$-$C_{11}$ cycloalkylalkyl, aryl, aryl($C_1$-$C_6$ alkyl)-, $C_1$-$C_6$ alkoxy and $C_2$-$C_5$ alkoxycarbonyl;

$R^2$ is H or $C_1$-$C_{10}$ alkyl;

$R^3$ and $R^4$ are independently selected from H, methyl, ethyl, propyl, butyl, pentyl or hexyl;

$R^5$ is selected from the group consisting of hydroxy, $C_1$-$C_{10}$ alkyloxy, $C_3$-$C_{11}$ cycloalkyloxy, $C_6$-$C_{10}$ aryloxy and $C_7$-$C_{11}$ arylalkyloxy;

$R^6$ is selected from the group consisting of H, $C_1$-$C_6$ alkyl, $C_2$-$C_6$ alkenyl, $C_2$-$C_6$ alkynyl, $C_3$-$C_7$ cycloalkyl, $C_1$–$C_8$ perfluoroalkyl, $C_7$–$C_{10}$ arylalkyloxy, $C_1$–$C_6$ alkoxy, aryloxy and aryl substituted with 0-2 $R^{6c}$;

$R^{6c}$ is H, halogen, $CF_3$, CN, $NO_2$, $NR^{6d}R^{6e}$, $C_1$–$C_8$ alkyl, $C_2$–$C_6$ alkenyl, $C_3$–$C_{11}$ cycloalkyl, $C_4$–$C_{11}$ cycloalkylalkyl, aryl, aryl($C_1$–$C_6$ alkyl)-, $C_1$–$C_6$ alkoxy, and $C_2$–$C_5$ alkoxycarbonyl; and $R^{6d}$ and $R^{6e}$ are independently selected from H or $C_1$–$C_{10}$ alkyl;

n is 1;

a is a single or double bond, with the proviso that if a is a double bond, it is not simultaneously substituted with $R^3$ and $R^4$;

said suitable pressure is up to 100 psi;

said hydrogenation catalyst is selected from the group consisting of palladium on carbon, palladium hydroxide on carbon, palladium on calcium carbonate and platinum on carbon;

said sufficient temperature is from about 50° C. to about 120° C.;

said sufficient time is from about 10 minutes to about 3 hours;

wherein an amount of catalyst loaded on carbon is from about 3% to about 5% by weight; and wherein an amount of a hydrogenation catalyst is from about 3% to about 7% by weight of compound (IV).

4. The process of claim 1, wherein:

$R^1$ is $NHR^{1a}$;

$R^{1a}$ is —C(=O)—O—$CH_2(CH_2)_2CH_3$ or 3,5-dimethyloxazol-4yl-sulfonyl;

$R^2$ is H;

$R^3$ and $R^4$ are H;

$R^5$ is methyl;

$R^6$ is selected from the group consisting of:
H, methyl, ethyl, propyl, butyl, pentyl, hexyl, $C_7$–$C_8$ arylalkyloxy, aryloxy, $C_1$–$C_5$ alkoxy and aryl;

n is 1, and a is a single bond;

said suitable pressure is from about 20 to about 50 psi;

said sufficient temperature is from about 50° C. to about 120° C.;

said sufficient time is from about 10 minutes to about 3 hours;

said hydrogenation catalyst is palladium on carbon;

wherein an amount of catalyst loaded on carbon is from about 3% to about 5% by weight; and wherein an amount of palladium on carbon is from about 3% to about 7% by weight of compound (IV).

* * * * *